United States Patent
Liu et al.

(10) Patent No.: US 9,278,925 B2
(45) Date of Patent: Mar. 8, 2016

(54) SUBSTITUTED 3-(BIPHENYL-3-YL)-4-HYDROXY-8-METHOXY-1-AZASPIRO[4.5]DEC-3-EN-2-ONE

(75) Inventors: Ningshu Liu, Berlin (DE); Kai Thede, Berlin (DE); Ursula Mönning, Woltersdorf (DE); Arne Scholz, Berlin (DE); Christoph-Stephan Hilger, Berlin (DE); Ulf Bömer, Glienicke (DE); Reiner Fischer, Moheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 46 days.

(21) Appl. No.: 14/236,279

(22) PCT Filed: Jul. 31, 2012

(86) PCT No.: PCT/EP2012/064974
§ 371 (c)(1),
(2), (4) Date: May 29, 2014

(87) PCT Pub. No.: WO2013/017600
PCT Pub. Date: Feb. 7, 2013

(65) Prior Publication Data
US 2014/0275199 A1    Sep. 18, 2014

(30) Foreign Application Priority Data

Aug. 4, 2011 (DE) .......................... 10 2011 080 406

(51) Int. Cl.
*C07D 207/18* (2006.01)
*C07D 209/54* (2006.01)
*A61K 31/403* (2006.01)

(52) U.S. Cl.
CPC ............ *C07D 209/54* (2013.01); *A61K 31/403* (2013.01)

(58) Field of Classification Search
CPC .................................................... C07D 207/18
See application file for complete search history.

(56) References Cited

U.S. PATENT DOCUMENTS

2010/0261608 A1* 10/2010 Fischer .................. A01N 43/38
504/283

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

* cited by examiner

*Primary Examiner* — Shawquia Jackson

(57) ABSTRACT

The invention relates to substituted 3-(biphenyl-3-yl)-4-hydroxy-8-methoxy-1-azaspiro[4.5]dec-3-en-2-ones, in particular for therapeutic purposes, to pharmaceutical compositions and to their use in therapy, in particular for the prophylaxis and therapy of neoplastic disorders.

8 Claims, 1 Drawing Sheet

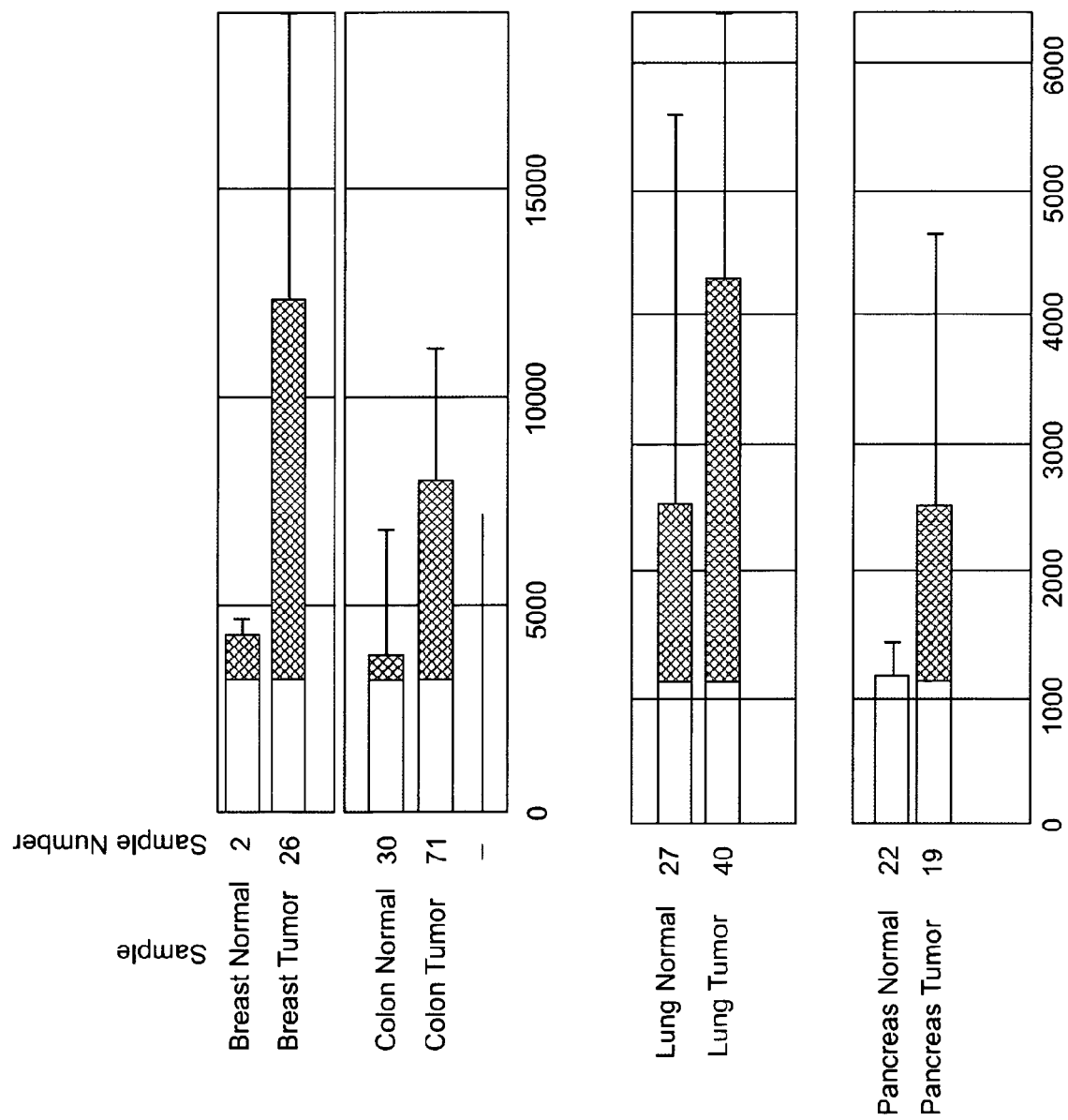

SUBSTITUTED 3-(BIPHENYL-3-YL)-4-HYDROXY-8-METHOXY-1-AZASPIRO[4.5]DEC-3-EN-2-ONE

The present invention relates to substituted 3-(biphenyl-3-yl)-4-hydroxy-8-methoxy-1-azaspiro[4.5]dec-3-en-2-ones, in particular for therapeutic purposes, to pharmaceutical compositions comprising the compounds according to the invention and to their use in therapy, in particular for the prophylaxis and/or therapy of neoplastic disorders.

Acetyl-CoA carboxylases (ACCs) play a key role in cellular fatty acid homeostasis. ACCs are biotin-containing enzymes which catalyze the carboxylation of acetyl-CoA to malonyl-CoA in an ATP-dependent manner (Kim, 1997; Harwood, 2005; Tong, 2005). This reaction, which proceeds as two half-reactions, a biotin carboxylase (BC) reaction and a carboxyltransferase (CT) reaction, is the first introductory step of fatty acid biosynthesis and is the rate-determining step of the pathway. Two human ACC isoforms, ACC1 and ACC2, which are encoded by two different genes, are known (LuTFI ABU-ELHEIGA et al, 1995, Jane WIDMER, et al. 1996). ACC1 is expressed in lipogenic tissue (liver, fatty tissue), localized in the cytosole and fills the malonyl-CoA pool which serves as C2 units donor for the de novo synthesis of long-chain fatty acids by FASN and subsequent chain extension. ACC2 is expressed mainly in oxidative tissues (liver, heart, skeletal muscle) (Bianchi et al., 1990; Kim, 1997), is associated with mitochondria and regulates a second malonyl-CoA pool. This regulates fatty acid oxidation by inhibiting carnitine palmityltransferase I, the enzyme which facilitates entry of long-chain fatty acids into the mitochondria for $\beta$ oxidation (Milgraum L Z, et al., 1997, Widmer J. et al., 1996). Both enzymes show very high sequence homology and are regulated in a similar manner by a combination of transcriptional, translational and posttranslational mechanisms. Both in humans and in animals, ACC activity is highly controlled by a number of dietary, hormonal and other physiological mechanisms such as forward allosteric activation by citrate, feedback inhibition by long-chain fatty acids, reversible phosphorylation and/or inactivation or modulation of enzyme production by modified gene expression.

ACC1 knockout mice are embryonically lethal (Swinnen, et al., 2006, Abu-Elheiga, et al. 2005). ACC2 knockout mice show reduced malonyl-CoA concentrations in skeletal and heart muscle, increased fatty acid oxidation in the muscle, reduced liver fat levels, reduced amounts of total body fat, increased levels of UCP3 in the skeletal muscle (as an indication of higher energy expenditure), a reduced body weight, reduced plasma concentrations of free fatty acids, reduced plasma glucose levels, reduced amounts of tissue glycogen, and they are protected against diet-induced diabetes and obesity (Abu-Elheiga et al., 2001, 2003; Oh et al., 2005).

In addition to the involvement in fatty acid synthesis in lipogenic tissues and fatty acid oxidation in oxidative tissues, in many tumour cells an upregulation of ACC and an increased lipogenesis was observed (Swinnen, et al., 2004, Heemers, et al., 2000, Swinnen, et al., 2002, Rossi, et al., 2003, Milgraum, et al., 1997, Yahagi, et al., 2005). With very high probability, this phenotype contributes to the development and progression of tumours; however, the regulatory mechanisms involved still have to be clarified.

EP0454782 and U.S. Pat. No. 5,759,837 protect the use of fatty acid synthesis inhibitors for inhibiting tumour cell growth. Cyclic ketoenols have not been disclosed.

A number of substances capable of inhibiting plant and/or insect ACC have been discovered.

The PCT patent application PCT/EP99/01787, published as WO 99/48869, which corresponds to the European Patent EP 1 066 258 B1, refers to novel arylphenyl-substituted cyclic ketoenols, to a plurality of processes for their preparation and to their use as pesticides and herbicides.

3-Acylpyrrolidine-2,4-diones have already been described as having pharmaceutical properties (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893 and EP-A-442 077) are known to have herbicidal, insecticidal or acaridical activity.

Also known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048545, DEA 102 00505 9892, WO 07/073856, WO 07/096058, WO 07/121868, WO 07/140881, WO 08/067873, WO 08/067910, WO 08/067911, WO 08/138551, WO 09/015801, WO 09/039975, WO 09/049851, WO 09/115262, WO10/052161, WO 10/063378, WO 10/063670, WO10/063380, WO10/066780, WO10/102758, WO2010/135914, WO2011/067131, WO2011/067135, WO2011/067203 and WO2011/067240).

Furthermore known are ketal-substituted 1H-arylpyrrolidine-2,4-diones from WO 99/16748 and (spiro)ketal-substituted N-alkoxyalkoxy-substituted arylpyrrolidinediones from JP-A-14 205 984 and Ito M. et. al., Bioscience, Biotechnology and Biochemistry 67, 1230-1238, (2003). Moreover, WO 06/024411 discloses herbicidal compositions comprising ketoenols.

WO 2008/022725 discloses 4'-biphenyl-substituted tetronic acid derivatives for the therapy of viral disorders.

WO 2005/089118 and WO2007/039286 disclose, in a general manner, nitrogen-containing bicyclic structures for therapy; however, 5'-biphenyl-substituted cyclic ketoenols are not specifically mentioned.

The structurally closest prior art may be represented by compounds having a methyl group instead of a trifluoromethyl group or a methoxymethyl group in position 8 of the azaspiro[4.5]dec-3-en-2-one ring system. Some of those compounds form part of the prior art and are disclosed, for example, in WO10/063378.

The structurally closest prior art may also be represented by compounds having a hydrogen atom instead of a methoxy group in position 8 of the azaspiro[4.5]dec-3-en-2-one ring system. Some of those compounds form part of the prior art and are disclosed, for example, in WO 07/048545 (Example I-1-a-5).

Here, WO10/063378 and WO 07/048545 relate to inventions in another field, namely the field of the herbicides.

Without exception, the closest structures of the prior art are known from the field of the herbicides, insecticides or fungicides. For these structures, it is firstly not known and secondly not foreseeable whether they inhibit human ACC. Even more so, it is unknown and unforeseeable for these structures whether they are selective against one of the human ACC isoforms.

Based on this prior art, it is an object of the present invention to provide structures for the therapy of human and veterinary disorders.

In particular, the structures according to the invention should be suitable for the prophylaxis and therapy of neoplastic disorders and have advantages over the structures known in the prior art.

What is to be provided are in particular structures for the therapy of disorders which strongly inhibit human ACC1. The structures sought should inhibit human ACC1 more strongly than human ACC2, that is they should be selective against human ACC2.

Preferably, the structures provided for the therapy of disorders should additionally also have one, even better more or best of all of the following properties:
  according to a single measurement or even better according to the mean of a plurality of measurements, they inhibit human ACC1 with an IC50 of less than 300 nM, even better less than 200 nM and even better still of less than 100 nM in the assay described,
  according to a single measurement or even better according to the mean of a plurality of measurements, they inhibit human ACC2 with an IC50 of greater than 0.5 µM, even better greater than 1.5 µM and even better still of greater than 2 µM in the assay described,
  according to a single measurement or even better according to the mean of a plurality of measurements, the ratio of the IC50 for the inhibition of human ACC2 to the IC50 for the inhibition of human ACC1 is at least a factor of 8, even better at least a factor of 15 and even better still at least a factor of 20.
  according to a single measurement or even better according to the mean of a plurality of measurements, they inhibit tumour cell proliferation of MCF7 cell lines with an IC50 of less than 250 nM, even better less than 100 nM and even better still of less than 50 nM in the assay described,
  according to a single measurement or even better according to the mean of a plurality of measurements, they have a logP/D value of less than 3, even better less than 2.5 in the assay described,
  according to a single measurement or even better according to the mean of a plurality of measurements, they have a logMA value of less than 3, even better less than 2.5, even better still less than 2 in the assay described,
  according to a single measurement or even better according to the mean of a plurality of measurements, they have an HSA protein binding constant of greater than 1 µmol/l in the assay described,
  according to a single measurement or even better according to the mean of a plurality of measurements, they have a free fraction of greater than 0.1%, even better greater than 0.2%, with respect to binding to human plasma protein in the assay described.
  according to a single measurement or even better according to the mean of a plurality of measurements, they have a ratio of the free fractions with respect to binding to mouse plasma protein and human plasma protein of a factor of less than 15, even better less than 10,
  they have a ratio of the free fractions with respect to plasma protein binding of various species which leads to an acceptable estimated human dose,
  they have pharmacokinetic parameters which lead to an acceptable estimated human dose and which allow administration as a medicament,
  they have low clearance,
  they have high bioavailability,
  they have a moderate to high distribution volume,
  they have an acceptable relative bioavailability which leads to an acceptable estimated human dose and which allows administration as a medicament,
  they have an estimated human half-life of not more than two weeks,
  they have an in-vivo activity in the PC3 xenograft mouse model,
  they have an activity in the PC3 xenograft mouse model with plasma levels which lead to an acceptable estimated human dose,
  their human daily dose estimated by the method described is less than 2 g, even better less than 1 g, per patient.

Surprisingly, it has now been found that compounds of the formula (I)

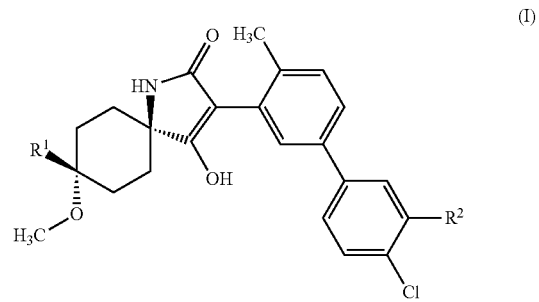

where
$R^1$ represents a trifluoromethyl or methoxymethyl group and
$R^2$ represents hydrogen or fluorine,
and their salts
are particularly suitable for the therapy of disorders and achieve the object of the invention.

Here, it was unforseeable whether and which of the structures known as insecticides or herbicides achieve the object of the invention, that is represents a structure which can be used in the therapy of human and/or animal disorders.

It was even less forseeable whether and which of the structures known as insecticides or herbicides inhibit human ACC, and even less whether and which shows selectivity against one of the human isoforms.

From the large group of the cyclic ketoenols known as insecticides, fungicides or herbicides, the compounds of the formula (I) surprisingly distinguish themselves by good enzyme inhibition of human ACC1. Here, the compounds according to the invention have increased selectivity against human ACC2 and inhibit in particular ACC1. This property was unforseeable and qualifies the compounds according to the invention for a therapy with reduced side effects. Unwanted side effects are probably caused by simultaneous inhibition of human ACC2s, whereas the effects are based mainly on the inhibition of human ACC1 s.

The selective against human ACC2 appears to be structurally based on the trans-methoxy group in position 8 of the azaspiro[4.5]dec-3-en-2-one ring system of the structures according to the invention. If this trans-methoxy group has already been realized in related structures of the prior art, it was unknown at the time of the invention if and with what kind of selectivity these structures inhibit human ACCs.

The present invention also embraces the use of the physiologically acceptable salts of the compounds according to the invention.

The present invention also embraces the use of the tautomeric forms of the compounds of the formula (I) according to the invention, for example muscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic sus-

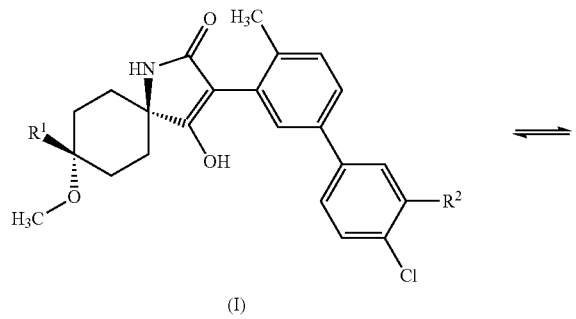 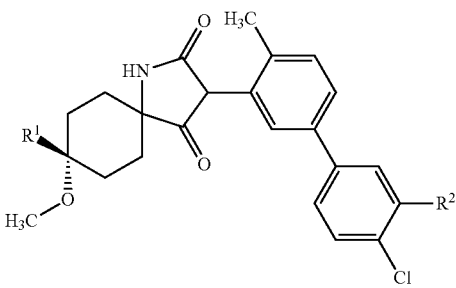

(I)

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The present invention furthermore provides medicaments comprising the compounds according to the invention and at least one or more further active compounds, in particular for the prophylaxis and/or therapy of neoplastic disorders.

The compounds according to the invention can act systemically and/or locally. For this purpose, it can be administered in a suitable manner, for example by the oral, parenteral, pulmonary, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intrapensions, ointments, creams, transdermal therapeutic systems (for example patches), milk, pastes, foams, dusting powders, implants or stents.

The compounds according to the invention can be converted to the administration forms mentioned. This can be accomplished in a manner known per se by mixing with inert nontoxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

The present invention furthermore provides medicaments which comprise the compounds according to the invention, typically together with one or more inert, nontoxic, pharmaceutically suitable auxiliaries, and the use thereof for the aforementioned purposes.

The formulation of the compounds according to the invention to give pharmaceutical preparations is effected in a manner known per se, by converting the active compound(s) to the desired administration form with the auxiliaries customary in pharmaceutical formulation.

The auxiliaries used may, for example, be carrier substances, fillers, disintegrants, binders, humectants, glidants, absorbents and adsorbents, diluents, solvents, cosolvents, emulsifiers, solubilizers, taste correctants, colorants, preservatives, stabilizers, wetting agents, salts for modifying osmotic pressure or buffers.

Reference should be made to Remington's Pharmaceutical Science, 15th ed. Mack Publishing Company, East Pennsylvania (1980).

The pharmaceutical formulations can be present
in solid form, for example as tablets, sugar-coated tablets, pills, suppositories, capsules, transdermal systems or
in semisolid form, for example as ointments, creams, gels, suppositories, emulsions or in liquid form, for example as solutions, tinctures, suspensions or emulsions.

The auxiliaries used in the context of the invention may, for example, be salts, saccharides (mono-, di-, tri-, oligo- and/or polysaccharides), proteins, amino acids, peptides, fats, waxes, oils, hydrocarbons and derivatives thereof, and the auxiliaries may be of natural origin or synthetic or partially synthetic.

Useful forms for oral or peroral administration are especially tablets, coated tablets, capsules, pills, powders, granules, pastilles, suspensions, emulsions or solutions.

Useful forms for parenteral administration are especially suspensions, emulsions, and particularly solutions.

The present invention relates to the compounds according to the invention.

They can be used for the prophylaxis and therapy of human disorders, in particular neoplastic disorders.

The compounds according to the invention can be used in particular for inhibiting or reducing cell proliferation and/or cell division and/or to induce apoptosis.

The compounds according to the invention are suitable in particular for the prophylaxis and/or therapy of hyper-proliferative disorders such as, for example,
 psoriasis,
 keloids and other skin hyperplasias,
 benign prostate hyperplasias (BPH),
 solid tumours and
 hematological tumours.

Solid tumours that can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones, and the connective tissue and metastases of these tumours.

Hematological tumours which can be treated are, for example,
 multiple myelomas
 lymphomas or
 leukemias
 Breast tumours which can be treated are, for example:
 breast carcinomas with positive hormone receptor status
 breast carcinomas with negative hormone receptor status
 Her-2 positive breast carcinomas
 hormone receptor and Her-2 negative breast carcinomas
 BRCA-associated breast carcinomas
 inflammatory breast carcinoma.
 Tumours of the respiratory tract which can be treated are, for example,
 non-small-cell bronchial carcinomas and
 small-cell bronchial carcinomas.
 Tumours of the brain which can be treated are, for example,
 gliomas,
 glioblastomas,
 astrocytomas,
 meningiomas and
 medulloblastomas.
 Tumours of the male reproductive organs which can be treated are, for example:
 prostate carcinomas,
 malignant testicular tumours and
 penis carcinomas.
 Tumours of the female reproductive organs which can be treated are, for example:
 endometrial carcinomas
 cervix carcinomas
 ovarial carcinomas
 vaginal carcinomas
 vulvar carcinomas
 Tumours of the gastrointestinal tract which can be treated are, for example:
 colorectal carcinomas
 anal carcinomas
 stomach carcinomas
 pancreas carcinomas
 esophagus carcinomas
 gall bladder carcinomas
 carcinomas of the small intestine
 salivary gland carcinomas
 neuroendocrine tumours
 gastrointestinal stroma tumours
 Tumours of the uorgenital tract which can be treated are, for example:
 urinary bladder carcinomas
 kidney cell carcinomas
 carcinomas of the renal pelvis and lower urinary tract
 Tumours of the eye which can be treated are, for example:
 retinoblastomas
 intraocular melanomas
 Tumours of the liver which can be treated are, for example:
 hepatocellular carcinomas
 cholangiocellular carcinomas
 Tumours of the skin which can be treated are, for example:
 malignant melanomas
 basaliomas
 spinaliomas
 Kaposi sarcomas
 Merkel cell carcinomas
 Tumours of the head and neck which can be treated are, for example:
 larynx carcinomas
 carcinomas of the pharynx and the oral cavity
 Sarcomas which can be treated are, for example:
 soft tissue sarcomas
 osteosarcomas
 Lymphomas which can be treated are, for example:
 non-Hodgkin lymphomas
 Hodgkin lymphomas
 cutaneous lymphomas
 lymphomas of the central nervous system
 AIDS-associated lymphomas
 Leukemias which can be treated are, for example:
 acute myeloid leukemias
 chronic myeloid leukemias
 acute lymphatic leukemias
 chronic lymphatic leukemias
 hairy cell leukemias Advantageously, the compounds according to the invention can be used for the prophylaxis and/or therapy of:
breast carcinomas, in particular hormone receptor-negative, hormone receptor-positive or BRCA-associated breast carcinomas, and also
pancreas carcinomas, renal cell carcinomas, hepatocellular carcinomas, malignant melanomas and other skin tumours, non-small-cell bronchial carcinomas, endometrial carcinoma, colorectal carcinomas and prostate carcinomas.

Particularly advantageously, the compounds according to the invention can be used for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

These disorders are well-characterized in man, but also exist in other mammals.

The present application provides the compounds of the formula (I) according to the invention, in particular the compounds:

(5r,8r)-3-(4'-chloro-3'-fluoro-4-methylbiphenyl-3-yl)-4-hydroxy-8-methoxy-8-(methoxymethyl)-1-azaspiro[4.5]dec-3-en-2-one (5r, 8r)-3-(4'-chloro-4-methylbiphenyl-3-yl)-4-hydroxy-8-methoxy-8-(methoxymethyl)-1-azaspiro[4.5]dec-3-en-2-one (5r, 8r)-3-(4'-chloro-3'-fluoro-4-methylbiphenyl-3-yl)-4-hydroxy-8-methoxy-8-(trifluoromethyl)-1-azaspiro[4.5]dec-3-en-2-one (5r, 8r)-3-(4'-chloro-4-methylbiphenyl-3-yl)-4-hydroxy-8-methoxy-8-(trifluoromethyl)-1-azaspiro[4.5]dec-3-en-2-one The present application further provides the compounds according to the invention for use as medicaments, especially for prophylaxis and/or therapy of neoplastic disorders.

The present application furthermore provides compounds according to the invention for the prophylaxis and/or therapy of breast carcinomas, pancreas carcinomas, renal cell carcinomas, hepatocellular carcinomas, malignant melanomas and other skin tumours, non-small-cell bronchial carcinomas, endometrial carcinomas, colorectal carcinomas or prostate carcinomas.

The present application furthermore provides compounds according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The invention furthermore provides for the use of the compounds according to the invention for preparing a medicament.

The present application furthermore provides for the use of the compounds according to the invention for preparing a medicament for the prophylaxis and/or therapy of neoplastic disorders.

The present application furthermore provides the use of the compounds according to the invention for preparing a medicament for the prophylaxis and/or therapy of breast carcinomas, pancreas carcinomas, renal cell carcinomas, hepatocellular carcinomas, malignant melanomas and other skin tumours, non-small-cell bronchial carcinomas, endometrial carcinomas, colorectal carcinomas or prostate carcinomas.

The present application furthermore provides the use of the compounds according to the invention for preparing a medicament for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The present application further provides for the use of the compound for prophylaxis and/or therapy of neoplastic disorders.

The present application furthermore provides the use of the compounds according to the invention for the prophylaxis and/or therapy of breast carcinomas, pancreas carcinomas, renal cell carcinomas, hepatocellular carcinomas, malignant melanomas and other skin tumours, non-small-cell bronchial carcinomas, endometrial carcinomas, colorectal carcinomas or prostate carcinomas.

The present application furthermore provides the use of the compounds according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The present application furthermore provides pharmaceutical formulations in the form of tablets comprising one of the compounds according to the invention for the prophylaxis and/or therapy of breast carcinomas, pancreas carcinomas, renal cell carcinomas, hepatocellular carcinomas, malignant melanomas and other skin tumours, non-small-cell bronchial carcinomas, endometrial carcinomas, colorectal carcinomas or prostate carcinomas.

The present application furthermore provides pharmaceutical formulations in the form of tablets comprising one of the compounds according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The invention furthermore provides for the use of the compounds according to the invention for treatment of disorders associated with proliferative processes.

The compounds according to the invention can be employed by themselves or, if required, in combination with one or more other pharmacologically active substances, as long as this combination does not lead to undesirable and unacceptable side effects. Accordingly, the present invention further provides medicaments comprising a compound according to the invention and one or more further active compounds, in particular for the prophylaxis and/or therapy of the disorders mentioned above.

For example, the compounds according to the invention can be combined with known antihyperproliferative, cytostatic or cytotoxic substances for treatment of cancer. The combination of the compounds according to the invention with other substances commonly used for cancer treatment, or else with radiotherapy, is particularly appropriate.

Examples of suitable combination active compounds include:
afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lapatinib, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, oraperd, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retic acid, satraplatin, seocalcitol, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations of these.

In a preferred embodiment, the compounds according to the invention can be combined with antihyperproliferative agents, examples of which are given in the following non-exhaustive list: aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenine, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

In a very promising manner, the compounds according to the invention can also be combined with biological therapeutics such as antibodies (for example Avastin, Rituxan, Erbitux, Herceptin) and recombinant proteins.

The compounds according to the invention can also achieve positive effects in combination with other therapies directed against angiogenesis, for example with Avastin, axitinib, regorafenib, recentin, sorafenib or sunitinib. Combinations with inhibitors of the proteasome and of mTOR, and also antihormones and steroidal metabolic enzyme inhibitors, are particularly suitable because of their favourable profile of side effects.

Generally, the following aims can be pursued with the combination of the compounds according to the invention with other cytostatically or cytotoxically active agents:
  improved efficacy in slowing the growth of a tumour, in reducing its size or even in the complete elimination thereof, compared with treatment with an individual active compound;
  the possibility of using the chemotherapeutics used in a lower dosage than in the case of monotherapy;
  the possibility of a more tolerable therapy with fewer side effects compared with individual administration;
  the possibility of treatment of a broader spectrum of tumours;
  the achievement of a higher rate of response to the therapy;
  a longer survival time of the patient compared with present-day standard therapy.

In addition, the compounds according to the invention can also be used in conjunction with radiotherapy and/or surgical intervention.

1. SYNTHESIS ROUTES FOR COMPOUNDS OF THE FORMULA (I)

The compounds of the formula (I) according to the invention can be prepared via synthesis routes A and/or B.

Synthesis Route A

An aryl bromide derivative of the formula (II)

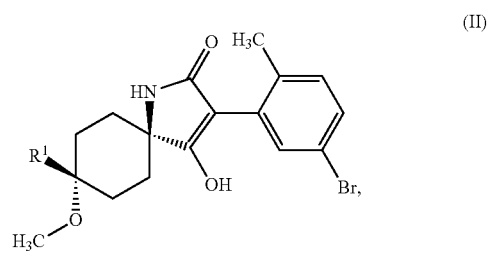

in which $R^1$ has the meaning given above is reacted in a Suzuki coupling with compounds of the formula (III)

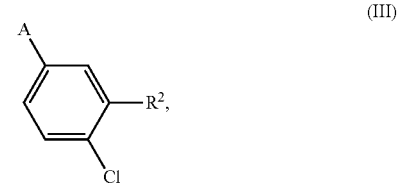

in which $R^2$ has the meaning given above and
A represents —B(OH)$_2$, a boronic ester, preferably boronic acid pinacol ester, or —BF$_3^-$K$^+$.

The Suzuki couplings are generally carried out in inert solvents, in the presence of a catalyst, if appropriate in the presence of an additional reagent, preferably in a temperature range of from room temperature to 130° C. at atmospheric pressure. The reactions can also be carried out in a closed vessel with heating in a microwave oven.

Catalysts are, for example, palladium catalysts customary for Suzuki reaction conditions; preference is given to catalysts such as dichlorobis(triphenylphosphine)palladium, tetrakistriphenylphosphinepalladium(0), palladium on carbon, palladium(II) acetate, palladium(II) acetate/tricyclohexylphosphine, palladium(II) acetoacetonate/tri-tert-butylphosphonium tetrafluoroborate, dichloro[1,1'-bis(diphenylphosphino)ferrocene]palladium/dichloromethane complex or palladium(II) acetate with a ligand such as dicyclohexyl[2',4',6'-tri(propan-2-yl)biphenyl-2-yl]phosphane.

Additional reagents are, for example, potassium acetate or caesium acetate, caesium carbonate, potassium carbonate or sodium carbonate, potassium tert-butoxide, caesium fluoride, potassium phosphate or sodium hydroxide or potassium hydroxide, preference is given to additional reagents such as caesium carbonate and/or aqueous sodium hydroxide solution.

Inert solvents are, for example, ethers such as dioxane, tetrahydrofuran or 1,2-dimethoxyethane, hydrocarbons such as benzene, xylene or toluene, or carboxamides such as dimethylformamide, dimethylacetamide or N-methylpyrrolidone, or alkyl sulphoxides such as dimethyl sulphoxide, or mixtures of the solvents with alcohols such as methanol or ethanol and/or water; preference is given to 1,2-dimethoxyethane.

The compounds of the formula (II) can be prepared by reacting compounds of the formula (IV)

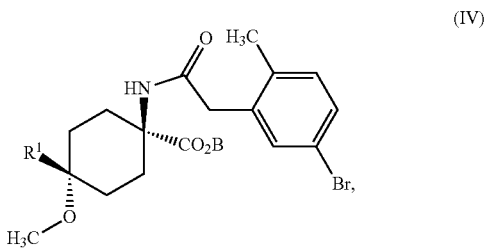

(IV)

in which $R^1$ has the meaning given above and
B represents C1-C6-alkyl, preferably ethyl or methyl,
under Dieckmann condensation conditions.

The Dieckmann condensations are generally carried out in inert solvents in the presence of a base, preferably in a temperature range from room temperature to 130° C. at atmospheric pressure. Bases are, for example, alkali metal alkoxides or alkaline earth metal alkoxides such as sodium tert-butoxide or potassium tert-butoxide, sodium methoxide or sodium ethoxide; preference is given to potassium tert-butoxide.

Inert solvents are, for example, ethers such as dioxane, tetrahydrofuran or 1,2-dimethoxyethane, hydrocarbons such as benzene, xylene or toluene, or carboxamides such as dimethylformamide, dimethylacetamide or N-methylpyrrolidone, or alkyl sulphoxides such as dimethyl sulphoxide, or alcohols such as methanol or ethanol; preference is given to dimethylformamide.

The compounds of the formula (IV) can be prepared by reacting compounds of the formula (V) or a salt of compounds of the formula (V)

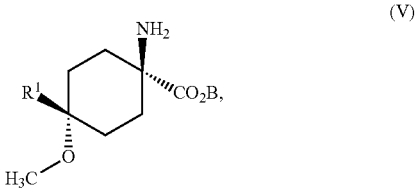

(V)

in which $R^1$ and B have the meanings given above with the compound of the formula (VI)

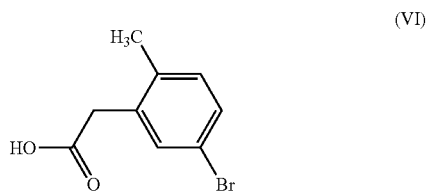

(VI)

under amide coupling conditions.

The reaction is generally carried out in inert solvents by reacting the compounds of the formula (VI) initially with thionyl chloride or an equivalent reagent known to the person skilled in the art and in the second step with compounds of the formula (V) or a salt of the compounds of the formula (V) in the presence of a base such as triethylamine or potassium carbonate.

In an alternative process, the reaction can be carried out in inert solvents in the presence of a dehydrating agent, if appropriate in the presence of a base, preferably in a temperature range from −30° C. to 50° C. at atmospheric pressure.

Inert solvents are, for example, halogenated hydrocarbons such as dichloromethane or trichloromethane, hydrocarbons, such as benzene or toluene, nitromethane, tetrahydrofuran, 1,4-dioxane, dimethylformamide or acetonitrile. It is also possible to use mixtures of the solvents. Particular preference is given to acetonitrile, dichloromethane, dimethylformamide, tetrahydrofuran or toluene.

Bases are, for example, alkali metal carbonates such as, for example, sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine.

Suitable dehydrating agents are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyl diimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol- 1-yloxytris(pyrrolidino)phosphonium hexafluorophosphate (PyBOP), or N-hydroxysuccinimide, or mixtures of these, with bases.

Preferably, the condensation is carried out with PyBOP, TBTU or with EDC in the presence of HOBt.

The process described above is illustrated by the synthesis scheme below:

Synthesis Route B

Alternatively, the compounds of the formula (I) according to the invention can be prepared by reacting a compound of the formula (VII)

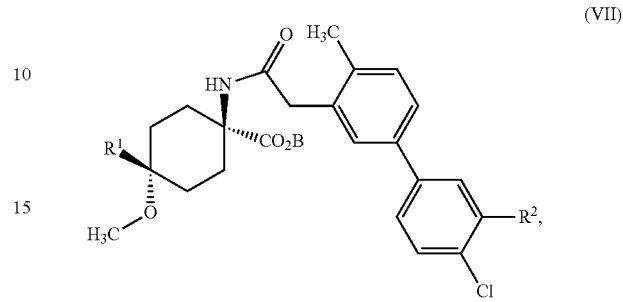

in which $R^1$, $R^2$ and B have the meanings given above under the conditions indicated above in a Dieckmann condensation.

The compounds of the formula (VII) can be prepared by reacting compounds of the formula (V) or a salt of compounds of the formula (V) in which $R^1$ and B have the meanings given above with compounds of the formula (VIII)

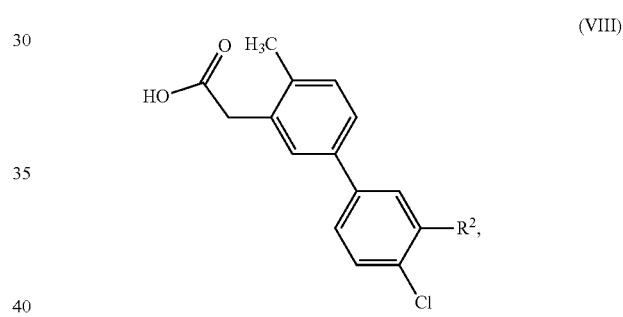

in which $R^2$ has the meaning given above under the amide coupling conditions indicated above.

The compounds of the formula (VIII) can be prepared by reacting the compound of the formula (VI) in a Suzuki reaction under the conditions indicated above with compounds of the formula (III) in which $R^2$ and A have the meanings given above.

The process described above is illustrated by the synthesis scheme below:

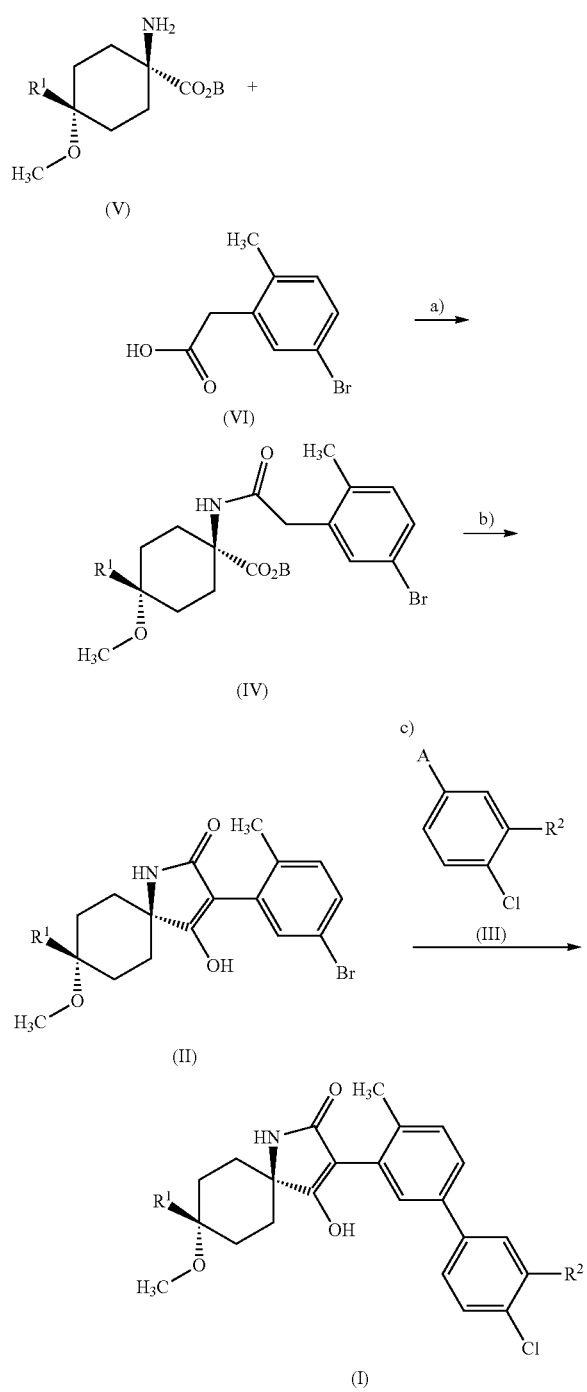

a): 1. SOCl$_2$, 80° C., 2. triethylamine, dichloromethane, room temperature;
b): KOtBu, DMF, 80° C.;
c): cat. dichloro[1,1'-bis(diphenylphosphino)ferrocene]palladium/dichloromethane complex, Cs$_2$CO$_3$, 1,2-dimethoxyethane/water, reflux.

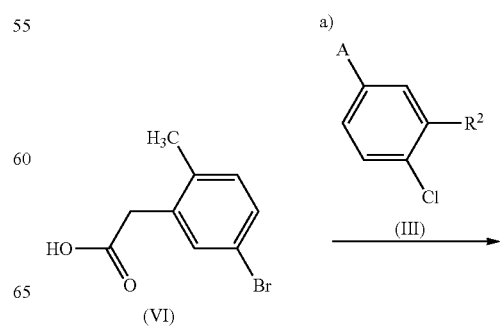

-continued

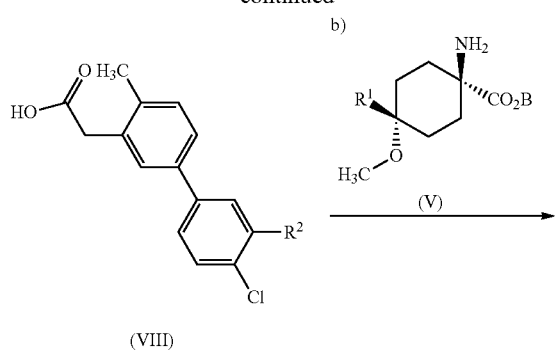

a): cat. palladium(II) acetylacetonate, cat. tri-tert-butylphosphonium tetrafluoroborate, NaOH, THF/water;
b): 1. SOCl$_2$, 80° C., 2. K$_2$CO$_3$, acetonitrile, room temperature;
c): KOtBu, DMF, room temperature.

The compounds of the formula (V) or salts of compounds of the formula (V) required for synthesis routes A and B, in which R$^1$ and B have the meanings given above, can be prepared by esterifying compounds of the formula (IX) or a salt of compounds of the formula (IX)

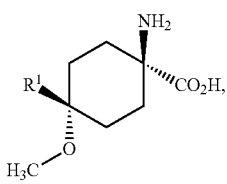

in which R$^1$ has the meaning given above by known processes, for example analogously to WO2002/02532 or WO2010/063378.

Compounds of the formula (IX) or salts of compounds of the formula (IX) in which R$^1$ has the meaning given above can be prepared by cleaving compounds of the formula (X)

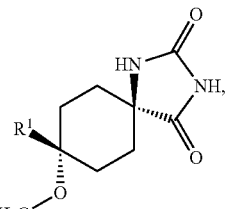

in which R$^1$ has the meaning given above by known processes, for example analogously to WO2002/02532 or WO2010/063378.

Compounds of the formula (X) in which R$^1$ has the meaning given above can be prepared by reacting compounds of the formula (XI)

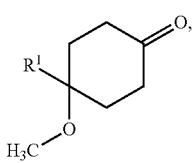

in which R$^1$ has the meaning given above by known processes in a Bucherer-Bergs reaction, for example analogously to WO2002/02532 or WO2010/063378. During the formation of the hydantoin of the formula (X), isomer mixtures of the cis isomer of the formula (X) and its trans isomer of the formula (X-a)

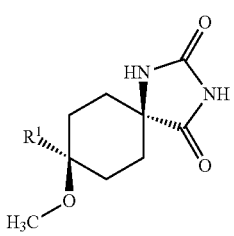

are obtained.

The trans isomer of the formula (X-a) can be separated off in this synthesis step. Alternatively, the isomer mixture can be reacted further and the respective trans-isomeric intermediate can be separated off in one of the further synthesis steps or from the end product of the formula (I).

Alternatively, using the Strecker synthesis, it is possible to prepare, by known processes, from the ketones of the formula (XI) aminonitriles which can be hydrolyzed by known processes to the amino acids of the formula (IX).

Compounds of the formula (XI) in which R$^1$ has the meaning given above can be prepared by subjecting compounds of the formula (XII)

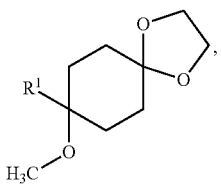
(XII)

in which R¹ has the meaning given above to a ketal cleavage (see Protective Groups in Organic Synthesis; Theodora W. Greene).

Compounds of the formula (XII) in which R¹ has the meaning given above can be prepared by methylating compounds of the formula (XIII)

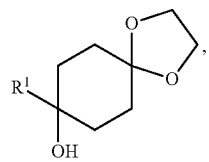
(XIII)

in which R¹ has the meaning given above by known processes, for example analogously to WO2010/063378.

The process described above is illustrated by the synthesis scheme below:

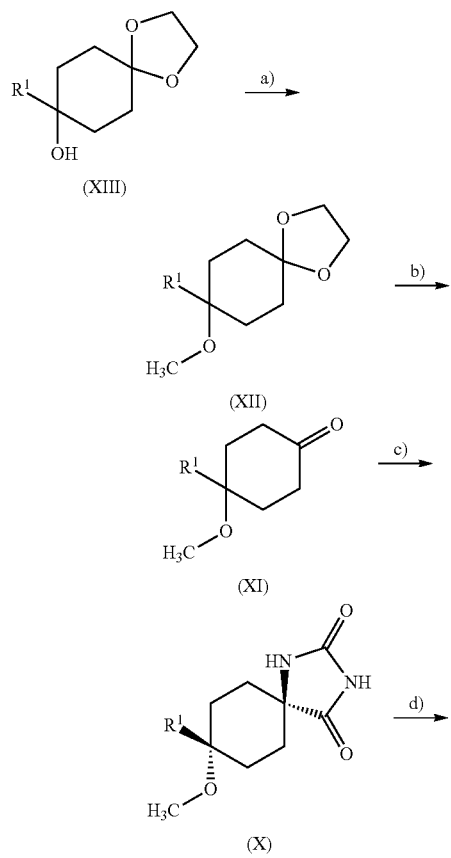

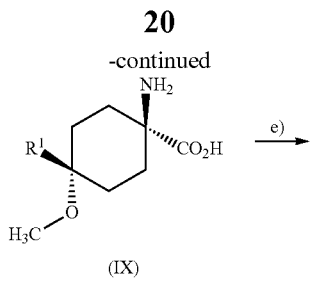
(IX)

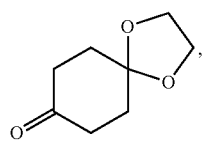
(V)

a): NaH, methyl iodide, THF, room temperature;
b): toluenesulphonic acid monohydrate, acetone/water;
c): NaCN, (NH₄)₂CO₃, water/ethanol, 60° C.;
d): KOH or NaOH, water, reflux;
e): SOCl₂, methanol, 40° C. to reflux.

The compound of the formula (XIII) in which R¹ represents a trifluoromethyl group can be prepared by reacting the compound of the formula (XIV)

(XIV)

with (trifluoromethyl)trimethylsilane.

The reaction of the ketone of the formula (XIV) with (trifluoromethyl)trimethylsilane to give the compounds of the formula (XIII) is generally carried out in inert solvents, in the presence of a catalyst, preferably in a temperature range of from −20° C. to 100° C. at atmospheric pressure. Catalysts are, for example, alkali metal or alkaline earth metal carbonates such as sodium carbonate, potassium carbonate or caesium carbonate. It is furthermore possible to employ alkali metal or alkaline earth metal fluorides such as lithium fluoride and caesium fluoride, and also fluoride salts of organic bases such as, for example, tetraethylammonium fluoride or tetrabutylammonium fluoride for catalyzing the desired reaction. Inert solvents are, for example, ethers such as dioxane, tetrahydrofuran or 1,2-dimethoxyethane, or carboxamides such as dimethylformamide, dimethylacetamide or N-methylpyrrolidone, or alkyl sulphoxides such as dimethyl sulphoxide; preference is given to dimethylformamide. The silyl derivatives of the formula (XIII) initially obtained are finally cleaved off by methods known to the person skilled in the art (see Protective Groups in Organic Synthesis; Theodora W. Greene).

The compound of the formula (XIII) in which R¹ represents a methoxymethyl group can be prepared by opening the epoxide of the formula (XV)

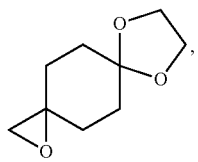

(XV)

by known processes, for example analogously to Rodriguez, Benjamin; Torre, Maria C. de la; Perales, Aurea; Malakov, Peter Y.; Papanov, Y.; et al., Tetrahedron, 1994, Volume 50, pages 5451-5468.

The epoxide of the formula (XV) is known and can be prepared from the compound of the formula (XIV) (Ciaccio, James A.; Drahus, Antoinette L.; Meis, Regina M.; Tingle, Carice T.; Smrtka, Michael; Geneste, Richard, Synthetic Communications, 2003, Volume 33, pages 2135-2144).

ABBREVIATIONS AND ACRONYMS

DMF dimethylformamide
DMSO dimethyl sulphoxide
ELSD evaporative light scattering detector
ESI electrospray ionization (in MS)
h hour(s)
HPLC high-pressure, high-performance liquid chromatography
LC-MS liquid chromatography-coupled mass spectrometry
min minute(s)
MS mass spectrometry
neg negative
NMR nuclear magnetic resonance spectrometry
pos positive
RP reversed-phase (in chromatography)
RT room temperature
$R_t$ retention time (in HPLC)
tert tertiary
THF tetrahydrofuran
UPLC ultra-performance liquid chromatography
LC-MS and HPLC Methods:
Method 1 (UPLC-MS):

Instrument: Waters Acquity UPLC-MS SQD 3001; column: Acquity UPLC BEH C18 1.7 50×2.1 mm; mobile phase A: water+0.1% formic acid, mobile phase B: acetonitrile; gradient: 0-1.6 min 1-99% B, 1.6-2.0 min 99% B; flow rate 0.8 ml/min; temperature: 60° C.; injection: 2 µl; DAD scan: 210-400 nM; ELSD.

Method 2 (UPLC-MS):

Instrument: Waters Acquity UPLC-MS SQD; column: Acquity UPLC BEH C18 1.7 50×2.1 mm; mobile phase A: water+0.05% formic acid, mobile phase B: acetonitrile+ 0.05% formic acid; gradient: 0-1.6 min 1-99% B, 1.6-2.0 min 99% B; flow rate 0.8 ml/min; temperature: 60° C.; injection: 2 µl; DAD scan: 210-400 nM; ELSD.

Method 3 (UPLC-MS):

Instrument: Waters Acquity UPLC-MS ZQ4000; column: Acquity UPLC BEH C18 1.7 50×2.1 mm; mobile phase A: water+0.05% formic acid, mobile phase B: acetonitrile+ 0.05% formic acid; gradient: 0-1.6 min 1-99% B, 1.6-2.0 min 99% B; flow rate 0.8 ml/min; temperature: 60° C.; injection: 2 µl; DAD scan: 210-400 nm

2. PREPARATION OF COMPARATIVE EXAMPLES AND WORKING EXAMPLES

Starting Compounds and Intermediates

Example 1A (4'-Chloro-3'-fluoro-4-methylbiphenyl-3-yl)acetic acid

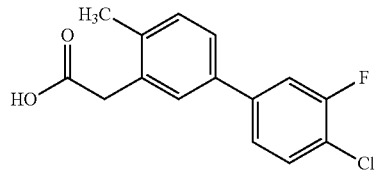 [SMILES: Cc1ccc(-c2ccc(Cl)c(F)c2)cc1CC(=O)O]

Under argon, 33.5 g (192 mmol) of (4-chloro-3-fluorophenyl)boronic acid were added to a solution of 40.0 g (175 mmol) of (5-bromo-2-methylphenyl)acetic acid (EP 1791816 and WO 2006/29799) in a mixture of 437 ml (437 mmol) of degassed 1N aqueous sodium hydroxide solution, 160 ml of degassed water and 160 ml of degassed tetrahydrofuran. The mixture was stirred for 10 minutes, 507 mg (1.75 mmol) of tri-tert-butylphosphonium tetrafluoroborate and 532 mg (1.75 mmol) of palladium(II) acetylacetonate were added and the mixture was stirred at room temperature for 20 h. Toluene and water were then added, the pH was adjusted to 1-2 with concentrated aqueous hydrogen chloride solution, the mixture was stirred for 10 minutes, the phases were separated, the aqueous phase was extracted twice with toluene and the combined organic phases were dried over sodium sulphate, filtered and concentrated. The residue was stirred in 300 ml of a 6/1 mixture of n-hexane/tert-butyl methyl ether for 30 minutes, filtered off with suction, washed with n-hexane and dried under reduced pressure. This gave 38.0 g (78% of theory) of the title compound.

$^1$H NMR (300 MHz, DMSO-$d_6$): δ [ppm]=2.27 (s, 3H), 3.67 (s, 2H), 7.27 (d, 1H), 7.49-7.59 (m, 3H), 7.61-7.75 (m, 2H), 12.4 (s, 1H).

LC-MS (Method 1): $R_t$=1.31 min; MS (ESIneg): m/z=277 [M−H]$^−$.

Example 2A (4'-Chloro-4-methylbiphenyl-3-yl)acetyl chloride

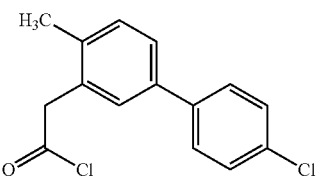 [SMILES: Cc1ccc(-c2ccc(Cl)cc2)cc1CC(=O)Cl]

5.00 g (19.18 mmol) of (4'-chloro-4-methylbiphenyl-3-yl) acetic acid (EP 2029531 A1 and US 2009/298828 A1) were dissolved in 36.51 g (306.84 mmol) of thionyl chloride. The reaction mixture was stirred at 80° C. for four hours and then concentrated under reduced pressure. Drying under fine vacuum gave 5.4 g (100% of theory) of the title compound as a brownish oil.

$^1$H NMR (300 MHz, CDCl$_3$): δ [ppm]=2.36 (s, 3H), 4.22 (s, 2H), 7.29 (d, 1H), 7.35-7.55 (m, 6H).

Example 3A (5-Bromo-2-methylphenyl)acetyl chloride

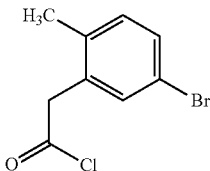

6.00 g (26.19 mmol) of (5-bromo-2-methylphenyl)acetic acid (EP 1791816 A1 and US 2006/29799 A1) were dissolved in 31.20 g (261.92 mmol) of thionyl chloride. The reaction mixture was stirred at 80° C. for two hours and then concentrated under reduced pressure. Drying under fine vacuum gave 6.29 g (97% of theory) of the title compound as a brownish oil.

$^1$H NMR (300 MHz, CDCl$_3$): δ [ppm]=2.26 (s, 3H), 4.12 (s, 2H), 7.09 (d, 1H), 7.34 (d, 1H), 7.37 (dd, 1H).

Example 4A (4'-Chloro-3'-fluoro-4-methylbiphenyl-3-yl)acetyl chloride

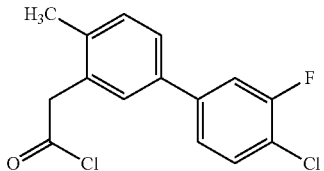 [SMILES: Cc1ccc(-c2ccc(Cl)c(F)c2)cc1CC(=O)Cl]

10.00 g (35.88 mmol) of (4'-chloro-3'-fluoro-4-methylbiphenyl-3-yl)acetic acid (Example 1A) were dissolved in 24.33 g (204.51 mmol) of thionyl chloride. The reaction mixture was stirred at 80° C. for one hour and then concentrated under reduced pressure. Drying under fine vacuum gave 10.54 g (99% of theory) of the title compound as a brownish oil.

$^1$H NMR (300 MHz, CDCl$_3$): δ [ppm]=2.36 (s, 3H), 4.22 (s, 2H), 7.26-7.39 (m, 4H), 7.41-7.49 (m, 2H).

Example 5A

Trimethyl {[8-(trifluoromethyl)-1,4-dioxaspiro[4.5]dec-8-yl]oxy}silane

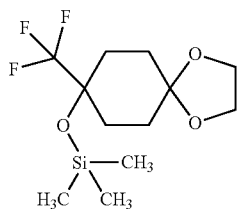

5.00 g (32.01 mmol) of 1,4-dioxaspiro[4.5]decan-8-one were dissolved in 50 ml of 1,2-dimethoxyethane, and 14.60 g (44.82 mmol) of caesium carbonate were added. At an internal temperature of under 30° C., 36.42 g (256.11 mmol) of trimethyl(trifluoromethyl)silane, dissolved in 100 ml of 1,2-dimethoxyethane, were added dropwise to the resulting suspension, and the reaction mixture was stirred at room temperature overnight. For work-up, about 600 ml of water were added dropwise to the reaction, and the target molecule was extracted with dichloromethane. The organic phase was washed repeatedly with water, dried over sodium sulphate and concentrated under reduced pressure. Drying gave 10.6 g (100% of theory) of the title compound as a brownish oil.

$^1$H NMR (400 MHz, DMSO-d$_6$): δ [ppm]=0.11 (s, 9H), 1.57-1.78 (m, 8H), 3.85 (s, 4H).

Example 6A 1,7,10-Trioxadispiro[2.2.4.2]dodecane

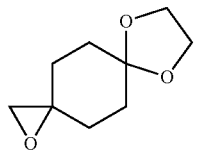 [SMILES: C1COC2(CCC3(CC2)CO3)O1]

A solution of 30.0 g (192 mmol) of 1,4-cyclohexanedione monoethylene acetal in 750 ml of dichloromethane was added to a homogeneous mixture of 50.7 g (231 mmol) of trimethylsulphoxonium iodide and 25.9 g (231 mmol) of potassium tert-butoxide, and the reaction mixture was stirred at room temperature for one hour. Ice-water was added, the phases were separated, the aqueous phase was extracted repeatedly with dichloromethane and the combined organic phases were washed repeatedly with water, dried over sodium sulphate, filtered and concentrated. This gave 28.3 g (87% of theory) of the title compound.

$^1$H NMR (400 MHz, DMSO-d$_6$): δ [ppm]=1.41-1.52 (m, 2H), 1.65-1.76 (m, 6H), 2.61 (s, 2H), 3.88 (s, 4H).

Example 7A 8-(Trifluoromethyl)-1,4-dioxaspiro[4.5]decan-8-ol

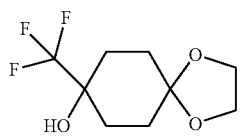 [SMILES: OC1(C(F)(F)F)CCC2(CC1)OCCO2]

At 0° C., 12.20 g (40.89 mmol) of trimethyl {[8-(trifluoromethyl)-1,4-dioxaspiro[4.5]dec-8-yl]oxy}silane (Example 5A) were dissolved in 164 ml of 1 molar tetrabutylammonium fluoride solution in tetrahydrofuran, and the mixture was stirred at room temperature for 3 hours. For work-up, about 600 ml of water were added to the reaction, and the target molecule was extracted with dichloromethane. The organic phase was washed repeatedly with water, dried over sodium sulphate and concentrated under reduced pressure. Drying gave 9.33 g (100% of theory) of the title compound as a brownish oil.

$^1$H NMR (400 MHz, DMSO-d$_6$): δ [ppm]=1.49-1.58 (m, 2H), 1.59-1.77 (m, 6H), 3.83 (s, 4H), 5.78 (s, 1H).

Example 8A 8-(Methoxymethyl)-1,4-dioxaspiro[4.5]decan-8-ol

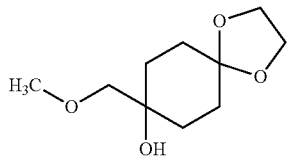

75 ml of a 25% strength methanolic sodium methoxide solution were added to 4.56 g (26.8 mmol) of the compound from Example 6A in 150 ml of methanol, and the mixture was stirred at 60° C. overnight. After cooling, the reaction mixture was concentrated and the residue was taken up in saturated aqueous ammonium chloride solution and extracted repeatedly with ethyl acetate. The combined organic phases were dried over sodium sulphate, filtered and concentrated. This gave 3.23 g (60% of theory) of the title compound.

$^1$H NMR (400 MHz, DMSO-$d_6$): δ [ppm]=1.37-1.47 (m, 4H), 1.50-1.63 (m, 2H), 1.68-1.80 (m, 2H), 3.10 (s, 2H), 3.25 (s, 3H), 3.82 (s, 4H), 4.24 (s, 1H).

Example 9A

8-Methoxy-8-(trifluoromethyl)-1,4-dioxaspiro[4.5]decane

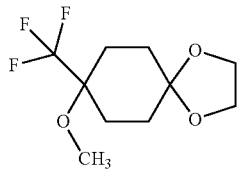 [SMILES: COC1(C(F)(F)F)CCC2(CC1)OCCO2]

At 0° C., 16.23 g (71.75 mmol) of 8-(trifluoromethyl)-1,4-dioxaspiro[4.5]decan-8-ol (Example 7A) were dissolved in 582 ml of tetrahydrofuran, 5.74 g (143.50 mmol) of sodium hydride (60% in paraffin oil) were added a little at a time and the mixture was stirred at room temperature for 1 hour. 50.92 g (358.76 mmol) of iodomethane were added dropwise to the resulting suspension, and the reaction mixture was stirred at room temperature overnight. For work-up, the mixture was poured into about 1 l of ice-water and the product was extracted with dichloromethane. The organic phase was washed repeatedly with water, dried over sodium sulphate and concentrated under reduced pressure. Drying gave 17.34 g (100% of theory) of the title compound as a brownish oil.

$^1$H NMR (300 MHz, DMSO-$d_6$): δ [ppm]=1.50-1.75 (m, 6H), 1.85-1.98 (m, 2H), 3.30 (s, 3H), 3.84 (s, 4H).

Example 10A

8-Methoxy-8-(methoxymethyl)-1,4-dioxaspiro[4.5]decane

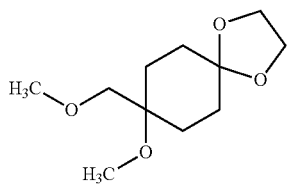

3.40 g (16.8 mmol) of the compound from Example 8A were dissolved in 170 ml of tetrahydrofuran, 1.01 g (25.2 mmol) of sodium hydride (60% in paraffin oil) were added and the mixture was stirred at room temperature for 0.5 hour. 3.58 g (25.2 mmol) of iodomethane were then added, and the reaction mixture was stirred at room temperature for two hours. 3.58 g (25.2 mmol) of iodomethane were then added, and the reaction mixture was stirred at room temperature for two hours. Water was added, the mixture was extracted repeatedly with ethyl acetate and the combined organic phases were dried over sodium sulphate, filtered and concentrated. This gave 3.35 g (92% of theory) of the title compound.

$^1$H NMR (300 MHz, DMSO-$d_6$): δ [ppm]=1.37-1.77 (m, 8H), 3.11 (s, 3H), 3.25 (s, 5H), 3.83 (s, 4H).

Example 11A

4-Methoxy-4-(trifluoromethyl)cyclohexanone

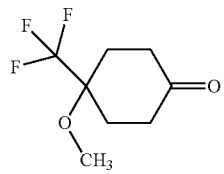

11.80 g (49.12 mmol) of 8-methoxy-8-(trifluoromethyl)-1,4-dioxaspiro[4.5]decane (Example 9A) were dissolved in 236 ml of acetone and 118 ml of water, 1.50 g (7.86 mmol) of 4-toluenesulphonic acid monohydrate were added and the mixture was heated at reflux overnight. The mixture was then poured into 1.2 l of water and the product was extracted with diethyl ether. The organic phase was washed with water, dried over sodium sulphate and concentrated under reduced pressure. The resulting residue was distilled under reduced pressure (boiling point: 106-110° C. at 40 mbar). This gave 6.86 g (71% of theory) of the title compound as a yellowish oil.

$^1$H NMR (300 MHz, CDCl$_3$): δ [ppm]=1.90-2.07 (m, 2H), 2.26-2.43 (m, 4H), 2.48-2.65 (m, 2H), 3.52 (s, 3H).

Example 12A

4-Methoxy-4-(methoxymethyl)cyclohexanone

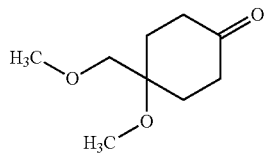

13.3 g (61.5 mmol) of the compound from Example 10A were dissolved in 200 ml of acetone and 100 ml of water, 1.87 g (9.84 mmol) of 4-toluenesulphonic acid monohydrate were added and the mixture was stirred at room temperature for two days. The acetone was then distilled off, the aqueous residue was neutralized by addition of sodium bicarbonate and 23.2 g of sodium chloride were added. The mixture was extracted repeatedly with ethyl acetate and the combined organic phases were washed with saturated aqueous sodium chloride solution, dried over sodium sulphate, filtered and concentrated. This gave 10.3 g (97% of theory) of the title compound.

$^1$H NMR (400 MHz, DMSO-$d_6$): δ [ppm]=1.61-1.76 (m, 2H), 1.97-2.12 (m, 4H), 2.34-2.46 (m, 2H), 3.22 (s, 3H), 3.28 (s, 3H), 3.36 (s, 2H).

Example 13A

8-Methoxy-8-methyl-1,3-diazaspiro[4.5]decane-2,4-dione

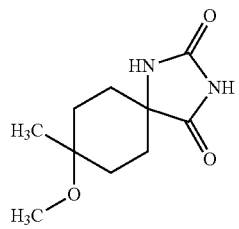

608 g (6.33 mol) of ammonium carbonate and 68.2 g (1.39 mmol) of sodium cyanide were dissolved in 2800 ml of water. 180 g (1.27 mmol) of 4-methoxy-4-methylcyclohexanone (described in WO 2010/063378) were added dropwise at room temperature, and the mixture was stirred at 60° C. overnight. The solid was filtered off with suction and dried. This gave 169.6 g (19% of theory) of the title compound as a 4/1 trans/cis diastereomer mixture which was reacted without further purification.

Example 14A

8-Methoxy-8-(trifluoromethyl)-1,3-diazaspiro[4.5]decane-2,4-dione

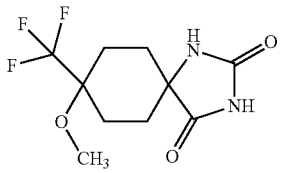 [SMILES: COC1(C(F)(F)F)CCC2(CC1)NC(=O)NC2=O]

8.80 g (44.86 mmol) of 4-methoxy-4-(trifluoromethyl)cyclohexanone (Example 11A), 4.40 g (89.72 mmol) of sodium cyanide and 17.24 g (179.44 mmol) of ammonium carbonate were suspended in 102 ml of ethanol and 102 ml of water. The resulting suspension was stirred at 60° C. for 20 hours. The precipitated product was filtered off, washed with water and dried under reduced pressure. This gave 10.05 g (84% of theory) of the title compound as a white powder.

$^1$H NMR (300 MHz, DMSO-$d_6$): δ [ppm]=1.38-2.20 (m, 8H), 3.31 (s, 3H), 7.87 (s, 0.25H), 8.70 (s, 0.75H), 10.64 (s, 1H).

Example 15A (5r,8r)-8-Methoxy-8-(methoxymethyl)-1,3-diazaspiro[4.5]decane-2,4-dione

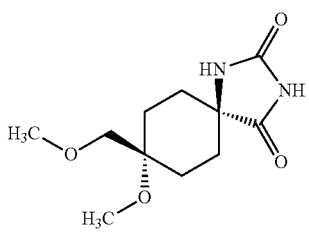 [SMILES: COC[C@]1(OC)CC[C@@]2(CC1)NC(=O)NC2=O]

28.6 g (298 mmol) of ammonium carbonate and 3.21 g (65.5 mmol) of sodium cyanide were dissolved in 130 ml of water. 10.3 g (59.5 mmol) of the compound from Example 12A were added dropwise at room temperature and the mixture was stirred at 60° C. overnight. The solid was filtered off with suction, washed with a little water and dried. This gave 8.67 g (60% of theory) of the title compound.

$^1$H NMR (400 MHz, DMSO-$d_6$): δ [ppm]=1.26-1.34 (m, 2H), 1.39-1.50 (m, 2H), 1.71-1.88 (m, 4H), 3.12 (s, 3H), 3.23 (s, 2H), 3.26 (s, 3H), 8.43 (s, 1H), 10.54 (s, 1H).

Example 16A

8-Methoxy-8-(methoxymethyl)-1,3-diazaspiro[4.5]decane-2,4-dione

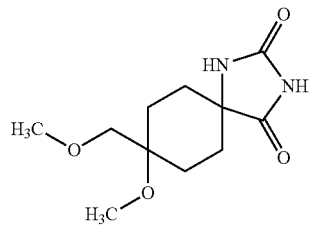 [SMILES: COCC1(OC)CCC2(CC1)NC(=O)NC2=O]

5.74 g (59.7 mmol) of ammonium carbonate and 1.46 g (29.8 mmol) of sodium cyanide were dissolved in 33 ml of water. 2.57 g (14.9 mmol) of a solution of the compound from Example 12A in 33 ml of ethanol were added dropwise at room temperature and the mixture was stirred at 60° C. overnight. The reaction mixture was concentrated to a quarter of its original volume and extracted repeatedly with dichloromethane and ethyl acetate, and the organic phases were dried over sodium sulphate, filtered and concentrated. This gave 675 mg (19% of theory) of the title compound as a diastereomer mixture which was reacted without further purification.

Example 17A

1-Amino-4-methoxy-4-methylcyclohexanecarboxylic acid hydrochloride

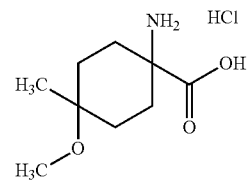

169.5 g of the compound from Example 13A in 970 ml of 30% strength aqueous potassium hydroxide solution were heated under reflux for 20 hours. After cooling, the reaction mixture was adjusted to pH 2 by addition of 670 ml of concentrated aqueous hydrogen chloride solution, the precipitate was filtered off with suction and the filtrate was concentrated. This gave 110.7 g of a crude product as a mixture of diastereomers which still contains salts and was reacted without further purification.

Example 18A

1-Amino-4-methoxy-4-(trifluoromethyl)cyclohexanecarboxylic acid

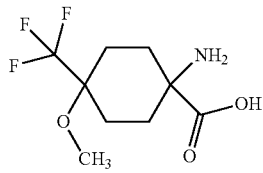 [SMILES: COC1(C(F)(F)F)CCC(N)(C(=O)O)CC1]

10.00 g (37.56 mmol) of 8-methoxy-8-(trifluoromethyl)-1,3-diazaspiro[4.5]decane-2,4-dione (Example 14A) were suspended in 125 ml of 3-molar aqueous sodium hydroxide solution and stirred under reflux conditions for 3 days. Subsequently, the pH was adjusted to 6 using concentrated aqueous hydrochloric acid, and the precipitated product was filtered off, washed with water and dried under reduced pressure. This gave 12.20 g (135% of theory; the product contains inorganic salts) of the title compound as a white powder.

$^1$H NMR (400 MHz, methanol-$d_4$): δ [ppm]=1.64-1.79 (m, 3.6H), 1.89-2.08 (m, 2.4H), 2.24-2.40 (m, 2H), 3.40 (q, 0.5H), 3.42 (q, 2.5H).

Example 19A trans-1-Amino-4-methoxy-4-(methoxymethyl)cyclohexanecarboxylic acid hydrochloride

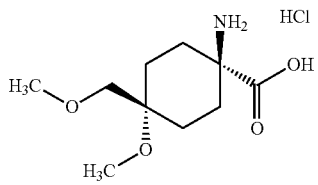

8.67 g (35.8 mmol) of the compound from Example 15A in 52 ml of 30% strength aqueous potassium hydroxide solution were heated under reflux for 36 hours. After cooling, the reaction mixture was concentrated to a quarter of its original volume, adjusted to pH 2 by addition of concentrated aqueous hydrogen chloride solution and evaporated to dryness. This gave 40.4 g of a crude product which still contains salts and was reacted without further purification.

$^1$H NMR (300 MHz, DMSO-$d_6$): δ [ppm]=1.57-1.77 (m, 6H), 1.87-2.05 (m, 2H), 3.08 (s, 3H), 3.23 (s, 3H), 3.27 (s, 2H), 8.50 (s, 3H).

Example 20A

1-Amino-4-methoxy-4-(methoxymethyl)cyclohexanecarboxylic acid hydrochloride

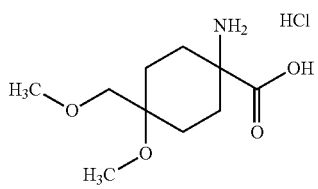

670 mg of the compound from Example 16A in 4 ml of 30% strength aqueous potassium hydroxide solution were heated under reflux for 18 hours. After cooling, the reaction mixture was concentrated to a quarter of its original volume, adjusted to pH 2 by addition of concentrated aqueous hydrogen chloride solution and concentrated. This gave 4.70 g of a crude product as a mixture of diastereomers which still contains salts and was reacted without further purification.

Example 21A

Methyl trans-1-amino-4-methoxy-4-methylcyclohexanecarboxylate hydrochloride

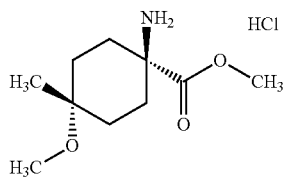

Under nitrogen and at 5° C., 172 ml (2.36 mol) of thionyl chloride were added dropwise to 110.5 g of the compound from Example 17A in 2500 ml of methanol. The mixture was stirred at 0° C. for 30 minutes and at 40° C. for 24 hours. After cooling, the solid was filtered off with suction, the filtrate was concentrated, the residue was stirred in a mixture of 1000 ml of methyl tert-butyl ether and 300 ml of acetonitrile for 10 minutes and the solid was filtered off with suction. This gave 37.1 g (12% of theory from 4-methoxy-4-methylcyclohexanone from Example 13A) of the title compound which was reacted without further purification.

$^1$H NMR (300 MHz, DMSO-$d_6$): δ [ppm]=1.08 (s, 3H), 1.60-1.79 (m, 6H), 1.94-2.11 (m, 2H), 3.07 (s, 3H), 3.75 (s, 3H), 8.68 (s, 3H).

Example 22A

Methyl 1-amino-4-methoxy-4-(trifluoromethyl)cyclohexanecarboxylate

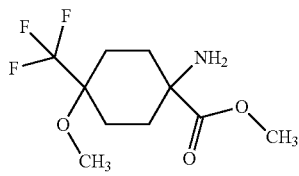

12.20 g (corresponds to about 37.58 mmol) of 1-amino-4-methoxy-4-(trifluoromethyl)cyclohexanecarboxylic acid (Example 18A) were suspended in 210 ml of methanol, and 10.4 ml (142.80 mmol) of thionyl chloride were added at 0° C. The mixture was boiled under reflux for 2 hours and cooled, another 10.4 ml (142.80 mmol) of thionyl chloride were added at 0° C. and the mixture was boiled under reflux for a further 2 hours. The reaction was cooled, another 10.4 ml (142.80 mmol) of thionyl chloride were added and the mixture was heated at reflux overnight until the reaction had gone to completion. For work-up, about 100 ml of methanol were distilled off and the concentrate was poured into 1 l of saturated aqueous sodium carbonate solution. The product was extracted with ethyl acetate and the organic phase was dried over sodium sulphate. Concentration by evaporation gave 7.01 g (73% of theory) of the title compound as a yellowish oil.

$^1$H NMR (400 MHz, DMSO-$d_6$): δ [ppm]=1.39-2.00 (m, 10H), 3.28 (q, 3H), 3.59 (s, 2.4H), 3.60 (s, 0.6H).

Example 23A

Methyl trans-1-amino-4-methoxy-4-(methoxymethyl)cyclohexanecarboxylate

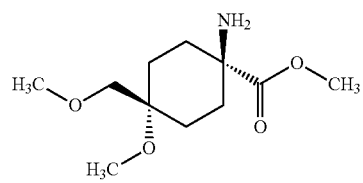

At 0° C., 34.8 ml (478 mmol) of thionyl chloride were added dropwise to 40.4 g of the compound from Example 19A in 400 ml of methanol. The mixture was stirred at 0° C. for 0.5 hours and at 40° C. for 24 hours. After cooling, the mixture was concentrated, the residue was taken up in ethyl acetate and washed with saturated aqueous sodium bicarbonate solution, the aqueous phase was extracted repeatedly with ethyl acetate and dichloromethane and the combined organic phases were dried over sodium sulphate, filtered and concentrated. This gave 7.16 g (87% of theory from Example 15A) of the title compound.

$^1$H NMR (400 MHz, DMSO-$d_6$): δ [ppm]=1.27-1.35 (m, 2H), 1.46-1.55 (m, 2H), 1.58-1.72 (m, 4H), 1.74-1.84 (m, 2H), 3.09 (s, 3H), 3.23 (s, 2H), 3.25 (s, 3H), 3.60 (s, 3H).

Example 24A

Methyl 1-amino-4-methoxy-4-(methoxymethyl)cyclohexanecarboxylate

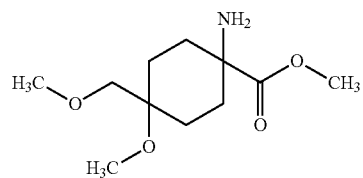

At 0° C., 4.1 ml (55.60 mmol) of thionyl chloride were added dropwise to 4.70 g of the compound from Example 20A in 50 ml of methanol. The mixture was stirred at 0° C. for 0.5 hours and at 40° C. overnight. After cooling, the mixture was concentrated, the residue was taken up in ethyl acetate and washed with saturated aqueous sodium bicarbonate solution, the aqueous phase was extracted repeatedly with ethyl acetate and the combined organic phases were dried over sodium sulphate, filtered and concentrated. This gave 392 mg (61% of theory from Example 16A) of the title compound as a diastereomer mixture which was reacted without further purification.

Example 25A

Methyl trans-1-{[(4'-chloro-4-methylbiphenyl-3-yl)acetyl]amino}-4-methoxy-4-methylcyclohexanecarboxylate

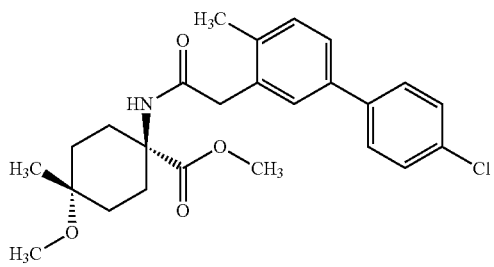 [SMILES: COC(=O)[C@]1(NC(=O)Cc2cc(-c3ccc(Cl)cc3)ccc2C)CC[C@](C)(OC)CC1]

8.08 g (31.0 mmol) of (4'-chloro-4-methylbiphenyl-3-yl)acetic acid (EP 2029531 A1 and US 2009/298828 A1) were dissolved in 12.9 ml (428 mmol) of thionyl chloride. The reaction mixture was stirred at 80° C. for 1 h and then concentrated. The residue was dissolved in 70 ml of acetonitrile. Ethyl acetate and saturated aqueous sodium bicarbonate solution were added to 6.00 g (25.2 mmol) of the compound from Example 21A. The phases were separated, the aqueous phase was extracted repeatedly with ethyl acetate and the combined organic phases were dried over sodium sulphate, filtered and concentrated. 120 ml of acetonitrile and 12.2 g (88.3 mmol) of potassium carbonate were added to the residue. With ice-cooling, the solution of the acid chloride was added dropwise, and the mixture was stirred at room temperature for two days. The mixture was then concentrated, the residue was taken up in water and extracted repeatedly with dichloromethane, and the combined organic phases were washed repeatedly with 1N aqueous hydrogen chloride solution and saturated aqueous sodium bicarbonate solution, dried over sodium sulphate, filtered and concentrated. The crude product was purified by chromatography on silica gel (mobile phase: hexane/ethyl acetate gradient). This gave 7.87 g (68% of theory) of the title compound.

$^1$H NMR (400 MHz, DMSO-$d_6$): δ [ppm]=0.98 (s, 3H), 1.34-1.46 (m, 2H), 1.54-1.64 (m, 2H), 1.74-1.87 (m, 4H), 2.28 (s, 3H), 3.04 (s, 3H), 3.51 (s, 3H), 3.58 (s, 2H), 7.23 (d, 1H), 7.43 (dd, 1H), 7.47-7.53 (m, 2H), 7.55 (d, 1H), 7.61-7.68 (m, 2H), 8.23 (s, 1H).

LC-MS (Method 2): $R_t$=1.41 min; MS (ESIpos): m/z=444 [M+H]$^+$.

Example 26A

Methyl cis-1-{[(4'-chloro-4-methylbiphenyl-3-yl)acetyl]amino}-4-(trifluoromethyl)cyclohexanecarboxylate

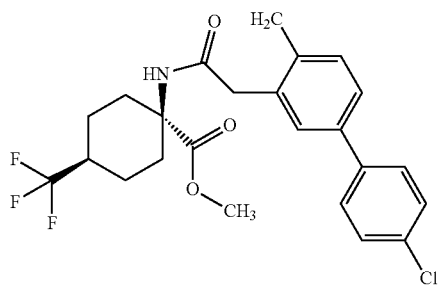 [SMILES: COC(=O)[C@]1(NC(=O)Cc2cc(-c3ccc(Cl)cc3)ccc2C)CC[C@@H](C(F)(F)F)CC1]

At room temperature, 5.00 g (19.09 mmol) of methyl cis-1-amino-4-(trifluoromethyl)cyclohexanecarboxylate hydrochloride (EP 1220841 A2 and WO 2001/23354 A3), 4.83 g (47.73 mmol) of triethylamine and 117 mg (0.955 mmol) of N,N-dimethylaminopyridine were dissolved in 40 ml of dichloromethane. A solution of 5.33 g (19.09 mmol) of (4'-chloro-4-methylbiphenyl-3-yl)acetyl chloride (Example 2A) in 40 ml of dichloromethane was then added dropwise to the mixture. The resulting reaction mixture was stirred at room temperature overnight. For work-up, the mixture was diluted with dichloromethane and the organic phase was washed with aqueous 5% strength citric acid. After drying over sodium sulphate, the mixture was concentrated by evaporation and the residue was purified by chromatography on silica gel (mobile phase: hexane/ethyl acetate gradient). Concentration and drying gave 6.36 g (71% of theory) of the title compound.

$^1$H NMR (300 MHz, DMSO-$d_6$): δ [ppm]=1.35-1.80 (m, 6H), 2.05-2.18 (m, 2H), 2.24 (s, 3H), 2.25-2.40 (m, 1H), 3.49 (s, 3H), 3.56 (s, 2H), 7.19 (d, 1H), 7.40 (dd, 1H), 7.42-7.52 (m, 3H), 7.56-7.65 (m, 2H), 8.34 (s, 1H).

LC-MS (Method 1): $R_t$=1.50 min; MS (ESIpos): m/z=468 [M+H]$^+$.

Example 27A

Methyl 8-{[(5-bromo-2-methylphenyl)acetyl]amino}-1,4-dioxaspiro[4.5]decane-8-carboxylate

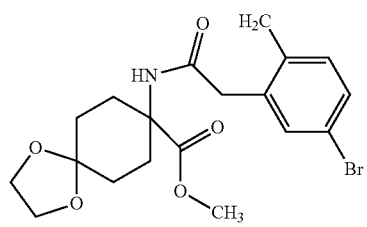 [SMILES: COC(=O)C1(NC(=O)Cc2cc(Br)ccc2C)CCC2(CC1)OCCO2]

At room temperature, 5.47 g (25.41 mmol) of methyl 8-amino-1,4-dioxaspiro[4.5]decane-8-carboxylate [T. Satoh et al., Tetrahedron 63 (2007), 4806-4813], 3.86 g (38.12 mmol) of triethylamine and 155 mg (1.27 mmol) of N,N-dimethylaminopyridine were dissolved in 45 ml of dichloromethane. A solution of 6.29 g (25.41 mmol) of (5-bromo-2-methylphenyl)acetyl chloride (Example 3A) in 45 ml of dichloromethane was then added dropwise to the mixture. The resulting reaction mixture was stirred at room temperature overnight. For work-up, the mixture was diluted with dichloromethane and the organic phase was washed with aqueous saturated sodium bicarbonate solution. After drying over sodium sulphate, the mixture was concentrated by evaporation and the residue was purified by chromatography on silica gel (mobile phase: hexane/ethyl acetate gradient/1% triethylamine) Evaporation and drying gave 3.64 g (34% of theory) of the title compound which was used without further characterization in the next step.

Example 28A

Methyl trans-1-{[(4'-chloro-3'-fluoro-4-methylbiphenyl-3-yl)acetyl]amino}-4-methoxy-4-methylcyclohexanecarboxylate

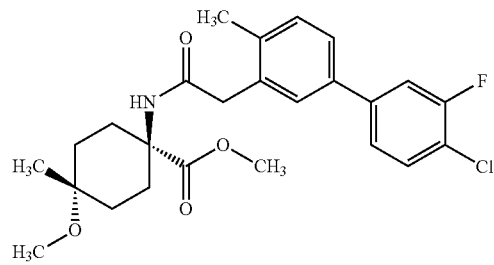 [SMILES: COC(=O)[C@]1(NC(=O)Cc2cc(-c3ccc(Cl)c(F)c3)ccc2C)CC[C@](C)(OC)CC1]

20.9 g (75.0 mmol) of the compound from Example 1A were dissolved in 31.2 ml (428 mmol) of thionyl chloride. The reaction mixture was stirred at 80° C. for 1 h and then concentrated. The residue was dissolved in 200 ml of acetonitrile. Ethyl acetate and saturated aqueous sodium bicarbonate solution were added to 16.0 g (67.3 mmol) of the compound from Example 21A. The phases were separated, the aqueous phase was extracted repeatedly with ethyl acetate and the combined organic phases were dried over sodium sulphate, filtered and concentrated. 250 ml of acetonitrile and 28.5 g (206 mmol) of potassium carbonate were added to the residue. With ice-cooling, the solution of the acid chloride was added dropwise, and the mixture was stirred at room temperature overnight. The mixture was then concentrated, the residue was taken up in water and extracted repeatedly with dichloromethane, and the combined organic phases were washed repeatedly with 1N aqueous hydrogen chloride solution and saturated aqueous sodium bicarbonate solution, dried over sodium sulphate, filtered and concentrated. For further purification, the residue was again taken up in dichloromethane, washed repeatedly with saturated aqueous sodium bicarbonate solution, dried over sodium sulphate, filtered and concentrated. This gave 23.6 g (76% of theory) of the title compound which were reacted without further purification.

$^1$H NMR (400 MHz, DMSO-$d_6$): δ [ppm]=0.98 (s, 3H), 1.32-1.45 (m, 2H), 1.55-1.63 (m, 2H), 1.74-1.86 (m, 4H), 2.29 (s, 3H), 3.04 (s, 3H), 3.52 (s, 3H), 3.58 (s, 2H), 7.24 (d, 1H), 7.46-7.55 (m, 2H), 7.59-7.73 (m, 3H), 8.23 (s, 1H).

LC-MS (Method 2): $R_t$=1.46 min; MS (ESIpos): m/z=462 [M+H]$^+$.

Example 29A

Methyl cis-1-{[(5-bromo-2-methylphenyl)acetyl]amino}-4-(trifluoromethyl)cyclohexanecarboxylate

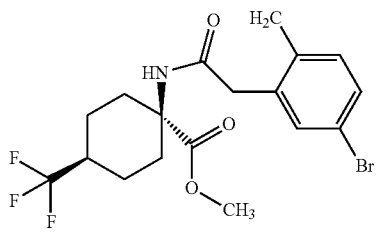 [SMILES: COC(=O)[C@]1(NC(=O)Cc2cc(Br)ccc2C)CC[C@@H](C(F)(F)F)CC1]

At room temperature, 10.00 g (38.22 mmol) of methyl cis-1-amino-4-(trifluoromethyl)cyclohexanecarboxylate hydrochloride (EP 1220841 A2 and WO 2001/23354 A3), 9.67 g (95.54 mmol) of triethylamine and 233 mg (1.91 mmol) of N,N-dimethylaminopyridine were dissolved in 95 ml of dichloromethane. A solution of 9.46 g (38.22 mmol) of (5-bromo-2-methylphenyl)acetyl chloride (Example 3A) in 95 ml of dichloromethane was then added dropwise to the mixture. The resulting reaction mixture was stirred at room temperature overnight. For work-up, the mixture was diluted with dichloromethane and the organic phase was washed with aqueous saturated sodium bicarbonate solution and with aqueous 5% strength citric acid. After drying over sodium sulphate, the mixture was concentrated by evaporation and the residue was purified by chromatography on silica gel (mobile phase: dichloromethane/methanol gradient). Evaporation and drying gave 8.84 g (53% of theory) of the title compound which was used without further characterization in the next step.

Example 30A

Methyl cis-1-{[(4'-chloro-4-methylbiphenyl-3-yl)acetyl]amino}-4-(methoxymethyl)cyclohexanecarboxylate

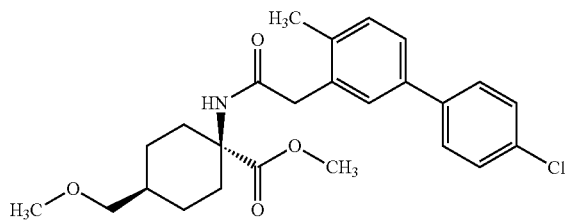 [SMILES: COC[C@H]1CC[C@](NC(=O)Cc2cc(-c3ccc(Cl)cc3)ccc2C)(C(=O)OC)CC1]

28.3 g (119 mmol) of methyl cis-1-amino-4-(methoxymethyl)cyclohexanecarboxylate hydrochloride (described in WO 2007/048545) were dissolved in 100 ml of water, 20.0 g (238 mmol) of sodium bicarbonate were added and the mixture was extracted repeatedly with ethyl acetate. The combined organic phases were dried over magnesium sulphate, filtered and concentrated. This gave 9.88 g of methyl cis-1-amino-4-(methoxymethyl)cyclohexanecarboxylate. 7.46 g (54.0 mmol) of potassium carbonate were added to 5.93 g (29.4 mmol) of methyl cis-1-amino-4-(methoxymethyl)cyclohexanecarboxylate in 50 ml of acetonitrile. With ice-cooling, a solution of 6.85 g (24.5 mmol) of the compound from Example 2A in 50 ml of acetonitrile was added dropwise, and the mixture was stirred at room temperature for one day. The mixture was then concentrated, the residue was taken up in water and extracted with dichloromethane, and the combined organic phases were washed with 1N aqueous hydrogen chloride solution and saturated aqueous sodium bicarbonate solution, dried over magnesium sulphate, filtered and concentrated. This gave 10.5 g of the title compound which were reacted without further purification.

$^1$H NMR (300 MHz, DMSO-$d_6$): δ [ppm]=1.05-1.25 (m, 2H), 1.44-1.65 (m, 5H), 2.01-2.12 (m, 2H), 2.28 (s, 3H), 3.04 (d, 2H), 3.17 (s, 3H), 3.51 (s, 3H), 3.58 (s, 2H), 7.23 (d, 1H), 7.43 (dd, 1H), 7.47-7.57 (m, 3H), 7.62-7.68 (m, 2H), 8.21 (s, 1H).

LC-MS (Method 1): $R_t$=1.43 min; MS (ESIpos): m/z=444 [M+H]$^+$.

Example 31A

Methyl cis-1-{[(5-bromo-2-methylphenyl)acetyl]amino}-4-(methoxymethyl)cyclohexanecarboxylate

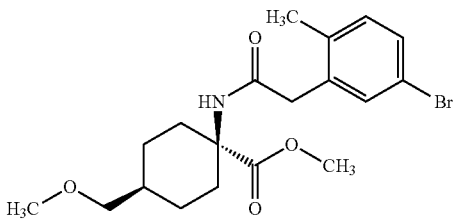 [SMILES: COC[C@H]1CC[C@](NC(=O)Cc2cc(Br)ccc2C)(C(=O)OC)CC1]

55.3 g (232 mmol) of methyl cis-1-amino-4-(methoxymethyl)cyclohexanecarboxylate hydrochloride (described in WO 2007/048545, page 144) were dissolved in 200 ml of water, 39.0 g (465 mmol) of sodium bicarbonate were added and the mixture was extracted repeatedly with ethyl acetate. The combined organic phases were dried over magnesium sulphate, filtered and concentrated. This gave 17.2 g of methyl cis-1-amino-4-(methoxymethyl)cyclohexanecarboxylate. 1.90 g (8.30 mmol) of (5-bromo-2-methylphenyl)acetic acid (described in EP 1791816 and WO 2006/29799) were dissolved in 3.5 ml (47.3 mmol) of thionyl chloride. The reaction mixture was stirred at 80° C. for 1 h and then concentrated. The residue was dissolved in 15 ml of acetonitrile. 2.52 g (18.2 mmol) of potassium carbonate were added to 2.00 g (9.94 mmol) of methyl cis-1-amino-4-(methoxymethyl)cyclohexanecarboxylate in 20 ml of acetonitrile. With ice-cooling, the solution of the acid chloride was added dropwise, and the mixture was stirred at room temperature for 24 h. The mixture was then concentrated, the residue was taken up in water and extracted with dichloromethane, and the combined organic phases were washed with 1N aqueous hydrogen chloride solution and saturated aqueous sodium bicarbonate solution, dried over magnesium sulphate, filtered and concentrated. This gave 3.11 g (91% of theory) of the title compound which were reacted without further purification.

$^1$H NMR (300 MHz, DMSO-$d_6$): δ [ppm]=1.07-1.29 (m, 2H), 1.47-1.66 (m, 5H), 2.01-2.12 (m, 2H), 2.20 (s, 3H), 3.13 (d, 2H), 3.22 (s, 3H), 3.51 (s, 3H), 3.54 (s, 3H), 7.10 (d, 1H), 7.30 (dd, 1H), 7.41 (d, 1H), 8.22 (s, 1H).

LC-MS (Method 1): $R_t$=1.25 min; MS (ESIpos): m/z=412 [M+H]$^+$.

Example 32A

Methyl 1-{[(4'-chloro-4-methylbiphenyl-3-yl)acetyl]amino}-4-methoxy-4-(trifluoromethyl)cyclohexanecarboxylate

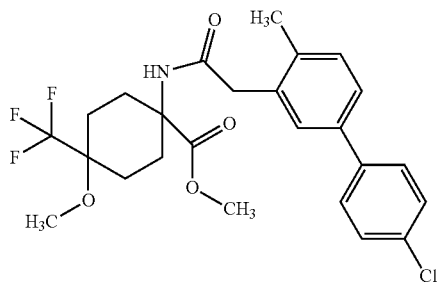 [SMILES: COC(=O)C1(NC(=O)Cc2cc(-c3ccc(Cl)cc3)ccc2C)CCC(OC)(C(F)(F)F)CC1]

3.94 g (15.44 mmol) of methyl 1-amino-4-methoxy-4-(trifluoromethyl)cyclohexanecarboxylate (Example 22A) and 1.56 g (15.44 mmol) of triethylamine were dissolved in 56 ml of dichloromethane. 3.92 g (14.03 mmol) of (4'-chloro-4-methylbiphenyl-3-yl)acetyl chloride (Example 2A), dissolved in 56 ml of dichloromethane, were added dropwise to this solution, and the reaction mixture was stirred at room temperature overnight. For work-up, the mixture was diluted with dichloromethane and the organic phase was washed with aqueous saturated sodium bicarbonate solution and with aqueous 1% strength citric acid. After drying over sodium sulphate, the organic phase was concentrated and the product was dried. This gave 6.81 g (97% of theory) of the title compound as a white powder.

LC-MS (Method 1): $R_t$=1.51 min; MS (ESIpos): m/z=498 [M+H]$^+$.

Example 33A

Methyl 1-{[(4'-chloro-3'-fluoro-4-methylbiphenyl-3-yl)acetyl]amino}-4-methoxy-4-(trifluoromethyl)cyclohexanecarboxylate

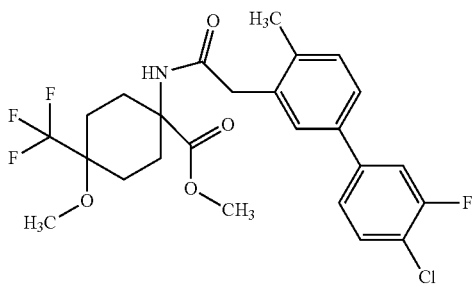 [SMILES: COC(=O)C1(NC(=O)Cc2cc(-c3ccc(Cl)c(F)c3)ccc2C)CCC(OC)(C(F)(F)F)CC1]

20.50 g (80.32 mmol) of methyl 1-amino-4-methoxy-4-(trifluoromethyl)cyclohexanecarboxylate (Example 22A) and 8.13 g (80.32 mmol) of triethylamine were dissolved in 280 ml of dichloromethane. 21.70 g (73.02 mmol) of (4'-chloro-3'-fluoro-4-methylbiphenyl-3-yl)acetyl chloride (Example 4AA), dissolved in 280 ml of dichloromethane, were added dropwise to this solution, and the reaction mixture was stirred at room temperature overnight. For work-up, the mixture was diluted with dichloromethane and the organic phase was washed with aqueous saturated sodium bicarbonate solution and with aqueous 1% strength citric acid. After drying over sodium sulphate, the organic phase was concentrated and the product was dried. This gave 37.05 g (98% of theory) of the title compound as a beige powder.

LC-MS (Method 1): $R_t$=1.51 min; MS (ESIpos): m/z=516 [M+H]$^+$.

Example 34A

Methyl trans-1-{[(4'-chloro-3'-fluoro-4-methylbiphenyl-3-yl)acetyl]amino}-4-methoxy-4-(methoxymethyl)cyclohexanecarboxylate

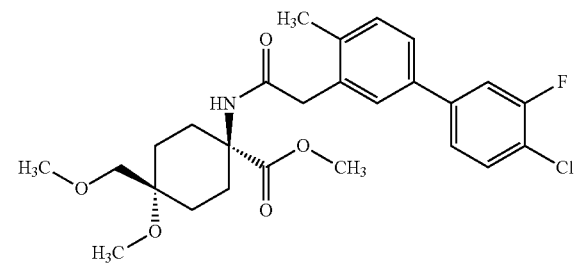 [SMILES: COC[C@]1(OC)CC[C@@](NC(=O)Cc2cc(-c3ccc(Cl)c(F)c3)ccc2C)(C(=O)OC)CC1]

4.48 g (16.1 mmol) of the compound from Example 1A were dissolved in 5.6 ml (76.4 mmol) of thionyl chloride. The reaction mixture was stirred at 80° C. for 1 h and then concentrated. The residue was dissolved in 20 ml of acetonitrile. 6.48 g (46.9 mmol) of potassium carbonate were added to 3.10 g (13.4 mmol) of the compound from Example 23A in 30 ml of acetonitrile. With ice-cooling, the solution of the acid chloride was added dropwise, and the mixture was stirred at room temperature overnight. The mixture was then added to ice-water and extracted repeatedly with dichloromethane, and the combined organic phases were washed repeatedly with 1N aqueous hydrogen chloride solution and saturated aqueous sodium bicarbonate solution, dried over sodium sulphate, filtered and concentrated. This gave 6.59 g (96% of theory) of the title compound which were reacted without further purification.

$^1$H NMR (300 MHz, DMSO-d$_6$): δ [ppm]=1.32-1.49 (m, 2H), 1.54-1.66 (m, 2H), 1.70-1.91 (m, 4H), 2.29 (s, 3H), 3.09 (s, 3H), 3.14 (s, 2H), 3.20 (s, 3H), 3.52 (s, 3H), 3.57 (s, 2H), 7.24 (d, 1H), 7.46-7.56 (m, 2H), 7.58-7.74 (m, 3H), 8.27 (s, 1H).

LC-MS (Method 2): $R_t$=1.38 min; MS (ESIpos): m/z=492 [M+H]$^+$.

Example 35A

Methyl 1-{[(4'-chloro-4-methylbiphenyl-3-yl)acetyl]amino}-4-methoxy-4-(methoxymethyl)cyclohexanecarboxylate

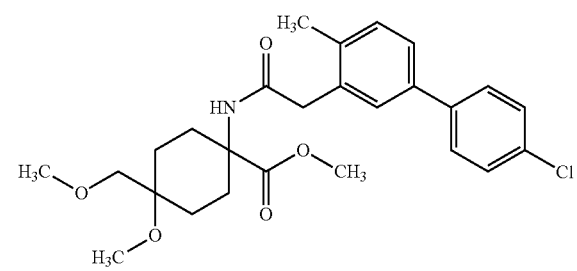 [SMILES: COCC1(OC)CCC(NC(=O)Cc2cc(-c3ccc(Cl)cc3)ccc2C)(C(=O)OC)CC1]

574 mg (2.20 mmol) of (4'-chloro-4-methylbiphenyl-3-yl)acetic acid (EP 2029531 A1 and US 2009/298828 A1) were dissolved in 0.9 g (12.5 mmol) of thionyl chloride. The reaction mixture was stirred at 80° C. for 1 h and then concentrated. The residue was dissolved in 5 ml of acetonitrile. 816 mg (5.90 mmol) of potassium carbonate were added to 390 mg (1.69 mmol) of the compound from Example 24A in 10 ml of acetonitrile. With ice-cooling, the solution of the acid chloride was added dropwise, and the mixture was stirred at room temperature overnight. The mixture was then concentrated, the residue was taken up in ice-water and extracted repeatedly with dichloromethane, and the combined organic phases were washed repeatedly with 1N aqueous hydrogen chloride solution and saturated aqueous sodium bicarbonate solution, dried over sodium sulphate, filtered and concentrated. This gave 570 mg of the title compound as a diastereomer mixture which were reacted without further purification.

LC-MS (Method 2): $R_t$=1.36 min; MS (ESIpos): m/z=474 [M+H]$^+$.

Example 36A

Methyl 1-{[(5-bromo-2-methylphenyl)acetyl]amino}-4-methoxy-4-(trifluoromethyl)cyclohexanecarboxylate

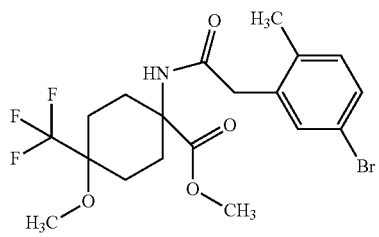

3.00 g (11.75 mmol) of methyl 1-amino-4-methoxy-4-(trifluoromethyl)cyclohexanecarboxylate (Example 22A) and 1.19 g (11.75 mmol) of triethylamine were dissolved in 40 ml of dichloromethane. 2.65 g (10.69 mmol) of (5-bromo-2-methylphenyl)acetyl chloride (Example 3A), dissolved in 40 ml of dichloromethane, were added dropwise to this solution, and the reaction mixture was stirred at room temperature overnight. For work-up, the mixture was diluted with dichloromethane and the organic phase was washed with aqueous saturated sodium bicarbonate solution and with aqueous 1% strength citric acid. After drying over sodium sulphate, the organic phase was concentrated and the product was dried. This gave 4.79 g (87% of theory) of the title compound as a beige powder.

LC-MS (Method 1): $R_t$=1.33 min; MS (ESIpos): m/z=468 [M+H]$^+$.

Example 37A (5s,8s)-3-(5-Bromo-2-methylphenyl)-4-hydroxy-8-(trifluoromethyl)-1-azaspiro[4.5]dec-3-en-2-one

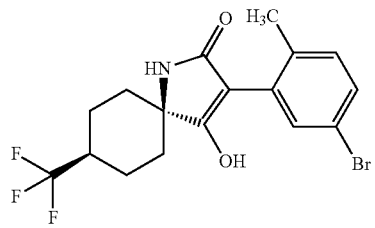 [SMILES: Cc1ccc(Br)cc1C1=C(O)[C@]2(CC[C@H](C(F)(F)F)CC2)NC1=O]

4.53 g (40.34 mmol) of potassium tert-butoxide were added to 8.80 g (20.17 mmol) of methyl cis-1-{[(5-bromo-2-methylphenyl)acetyl]amino}-4-(trifluoromethyl)cyclohexanecarboxylate (Example 29A) in 100 ml of N,N-dimethylformamide. The reaction mixture was stirred at 80° C. for 60 minutes. For work-up, the cold reaction mixture was poured into 800 ml of ice-water and acidified with aqueous hydrochloric acid. The crude product was filtered off and purified by chromatography on silica gel (mobile phase: hexane/ethyl acetate gradient). Drying gave 5.23 g (64% of theory) of the title compound.

$^1$H NMR (400 MHz, DMSO-d$_6$): δ [ppm]=1.40-1.50 (m, 2H), 1.58-1.72 (m, 2H), 1.77-1.86 (m, 2H), 1.86-1.96 (m, 2H), 2.07 (s, 3H), 2.12-2.28 (m, 1H), 7.14 (d, 1H), 7.19 (d, 1H), 7.33 (dd, 1H), 8.33 (s, 1H), 11.01 (s, 1H).

LC-MS (Method 3): $R_t$=1.18 min; MS (ESIpos): m/z=406 [M+H]$^+$.

Example 38A 11-(5-Bromo-2-methylphenyl)-12-hydroxy-1,4-dioxa-9-azadispiro[4.2.4.2]tetradec-11-en-10-one

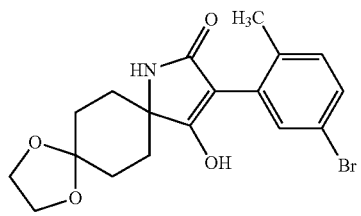 [SMILES: Cc1ccc(Br)cc1C1=C(O)C2(CCC3(CC2)OCCO3)NC1=O]

1.92 g (17.08 mmol) of potassium tert-butoxide were added to 3.64 g (8.54 mmol) of methyl 8-{[(5-bromo-2-methylphenyl)acetyl]amino}-1,4-dioxaspiro[4.5]decane-8-carboxylate (Example 27A) in 43 ml of N,N-dimethylformamide. The reaction mixture was stirred at 80° C. for 30 minutes. For work-up, the cold reaction mixture was poured into 500 ml of ice-water and acidified to pH=4 with aqueous hydrochloric acid. The crude product was filtered off. Drying gave 2.49 g (74% of theory) of the title compound which was used without further characterization in the next step.

Example 39A 3-(5-Bromo-2-methylphenyl)-4-hydroxy-1-azaspiro[4.5]dec-3-ene-2,8-dione

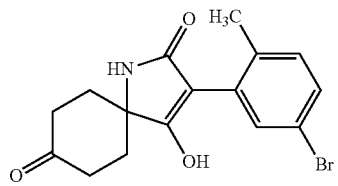 [SMILES: Cc1ccc(Br)cc1C1=C(O)C2(CCC(=O)CC2)NC1=O]

192 mg (1.01 mmol) of 4-toluenesulphonic acid monohydrate were added to 2.49 g (6.32 mmol) of 11-(5-bromo-2-methylphenyl)-12-hydroxy-1,4-dioxa-9-azadispiro[4.2.4.2]tetradec-11-en-10-one (Example 38A) in 26 ml of acetone and 13 ml of water. The reaction mixture was stirred at 80° C. overnight. For work-up, the cold reaction mixture was diluted with water and acetone was removed on a rotary evaporator. The precipitated crude product was extracted with ethyl acetate. The organic phase was washed with saturated aqueous sodium chloride solution, dried over sodium sulphate and concentrated under reduced pressure. Drying gave 1.97 g (89% of theory) of the title compound.

$^1$H NMR (400 MHz, DMSO-$d_6$): δ [ppm]=1.68-1.78 (m, 2H), 2.09 (s, 3H), 2.21-2.34 (m, 4H), 2.64-2.78 (m, 2H), 7.15 (d, 1H), 7.23 (d, 1H), 7.35 (dd, 1H), 8.53 (s, 1H), 11.12 (s, 1H).

LC-MS (Method 3): $R_t$=0.87 min; MS (ESIpos): m/z=352 [M+H]$^+$.

Example 40A (5r,8r)-3-(5-Bromo-2-methylphenyl)-4,8-dihydroxy-8-(trifluoromethyl)-1-azaspiro[4.5]dec-3-en-2-one

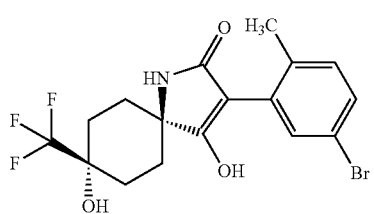 [SMILES: Cc1ccc(Br)cc1C1=C(O)[C@]2(CC[C@](O)(C(F)(F)F)CC2)NC1=O]

521 mg (1.60 mmol) of caesium carbonate and 975 mg (6.85 mmol) of (trifluoromethyl)trimethylsilane were added to 400 mg (1.14 mmol) of 3-(5-bromo-2-methylphenyl)-4-hydroxy-1-azaspiro[4.5]dec-3-ene-2,8-dione (Example 39A) in 8.3 ml of N,N-dimethylformamide. The reaction mixture was stirred at room temperature for three hours. Subsequently, the mixture was diluted with water, acidified to pH=4.5 with aqueous citric acid and extracted with ethyl acetate. The organic phase was washed with water, dried over sodium sulphate and concentrated under reduced pressure. The residue was dissolved in 5 ml of tetrahydrofuran, 1 ml of 4N aqueous hydrochloric acid was added and the mixture was stirred at room temperature for one hour and then diluted with water. The crude product was extracted with ethyl acetate and the organic phase was dried over sodium sulphate. Following concentration under reduced pressure, the residue was purified by chromatography on silica gel (mobile phase: hexane/ethyl acetate gradient). Evaporation and drying gave 367 mg (76% of theory) of the title compound.

$^1$H NMR (400 MHz, methanol-$d_4$): δ [ppm]=1.39-1.50 (m, 2H), 1.84-1.98 (m, 4H), 2.15 (s, 3H), 2.30-2.43 (m, 2H), 7.15 (d, 1H), 7.27 (d, 1H), 7.34 (dd, 1H).

LC-MS (Method 1): $R_t$=0.96 min; MS (ESIpos): m/z=420 [M+H]$^+$.

Example 41A (5s,8s)-3-(5-Bromo-2-methylphenyl)-4-hydroxy-8-(methoxymethyl)-1-azaspiro[4.5]dec-3-en-2-one

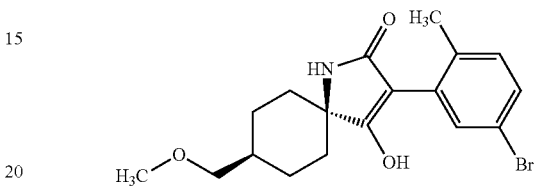

1.69 g (15.1 mmol) of potassium tert-butoxide were added to 3.11 g (7.54 mmol) of the compound from Example 31A in 11 ml of N,N-dimethylformamide. The reaction mixture was heated at 80° C. for 15 minutes. After cooling, the mixture was concentrated, the residue was taken up in water, 1N aqueous hydrogen chloride solution was added dropwise and the mixture was stirred for 0.5 h. The precipitate was filtered off with suction, washed with water and dried. This gave 2.83 g (96% of theory) of the title compound.

$^1$H NMR (300 MHz, DMSO-$d_6$): δ [ppm]=1.22-1.44 (m, 4H), 1.46-1.63 (m, 1H), 1.65-1.75 (m, 2H), 1.80-1.85 (m, 2H), 2.11 (s, 3H), 3.15 (d, 2H), 3.23 (s, 3H), 7.17 (d, 1H), 7.22 (d, 1H), 7.36 (dd, 1H), 8.16 (s, 1H), 10.89 (s, 1H).

LC-MS (Method 1): $R_t$=1.05 min; MS (ESIpos): m/z=380 [M+H]$^+$.

Example 42A 3-(5-Bromo-2-methylphenyl)-4-hydroxy-8-methoxy-8-(trifluoromethyl)-1-azaspiro[4.5]dec-3-en-2-one

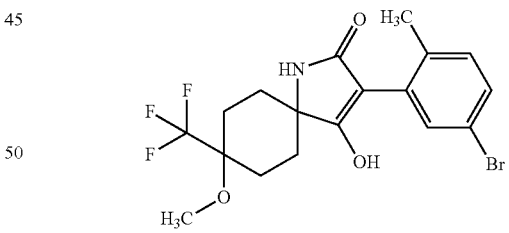

2.26 g (20.16 mmol) of potassium tert-butoxide were added to 4.70 g (10.08 mmol) of methyl 1-{[(5-bromo-2-methylphenyl)acetyl]amino}-4-methoxy-4-(trifluoromethyl)cyclohexanecarboxylate (Example 36A) in 50 ml of N,N-dimethylformamide. The reaction mixture was stirred at 80° C. for 60 minutes. For work-up, the cold reaction mixture was poured into 800 ml of ice-water and acidified with aqueous hydrochloric acid. The crude product was filtered off and dried. This gave 3.68 g (84% of theory) of the title compound as a beige powder.

$^1$H NMR (400 MHz, methanol-$d_4$): δ [ppm]=1.39-2.45 (m, 11H), 3.42-3.46 (m, 3H), 7.12-7.18 (m, 1H), 7.25-7.29 (m, 1H), 7.32-7.38 (m, 1H).

COMPARATIVE EXAMPLES

For Working Example 1-1

V.1-a (=Compound of Table 1, Row 20, p. 40 of WO10/063378)

(5r,8r)-3-(4'-Chloro-4-methylbiphenyl-3-yl)-4-hydroxy-8-methoxy-8-methyl-1-azaspiro[4.5]dec-3-en-2-one

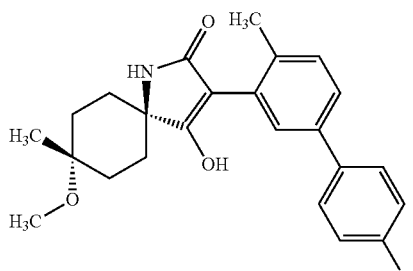

Under nitrogen 2.18 g (19.4 mmol) of potassium tert-butoxide were added to 7.83 g (17.6 mmol) of the compound from Example 25A in 75 ml of N,N-dimethylformamide. The reaction mixture was stirred at room temperature for 15 minutes. The mixture was then concentrated, the residue was taken up in ice-water and acidified with 1N aqueous hydrogen chloride solution, the mixture was stirred for 30 minutes and filtered off with suction and the precipitate was washed with water and dried. For further purification, the product was dissolved in 1N aqueous sodium hydroxide solution, the mixture was filtered, and the product was precipitated by acidification with aqueous 1 N hydrochloric acid, washed with water, filtered off and dried. This gave 4.78 g (65% of theory) of the title compound.

$^1$H NMR (400 MHz, DMSO-$d_6$): δ [ppm]=1.09 (s, 3H), 1.12-1.20 (m, 2H), 1.60-1.71 (m, 2H), 1.71-1.80 (m, 2H), 2.04-2.14 (m, 2H), 2.18 (s, 3H), 3.10 (s, 3H), 7.30 (d, 1H), 7.34 (d, 1H), 7.46-7.52 (m, 3H), 7.62-7.68 (m, 2H), 8.15 (s, 1H), 10.79 (s, 1H).

LC-MS (Method 2): $R_t$=1.23 min; MS (ESIpos): m/z=412 [M+H]$^+$.

V.1-b (5s,8s)-3-(4'-Chloro-4-methylbiphenyl-3-yl)-4-hydroxy-8-(trifluoromethyl)-1-azaspiro[4.5]dec-3-en-2-one

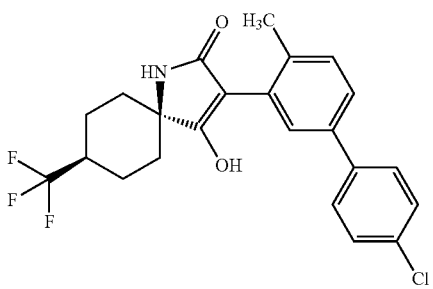 [SMILES: Cc1ccc(-c2ccc(Cl)cc2)cc1C1=C(O)[C@]2(CC[C@H](C(F)(F)F)CC2)NC1=O]

3.05 g (27.18 mmol) of potassium tert-butoxide were added to 6.36 g (13.59 mmol) of methyl cis-1-{[(4'-chloro-4-methylbiphenyl-3-yl)acetyl]amino}-4-(trifluoromethyl)cyclohexanecarboxylate (Example 26A) in 68 ml of N,N-dimethylformamide. The reaction mixture was stirred at 80° C. for 60 minutes. For work-up, the cold reaction mixture was poured into 800 ml of ice-water and acidified with aqueous hydrochloric acid. The crude product was filtered off, dried and purified by chromatography on silica gel (hexane/ethyl acetate gradient). Evaporation gave 4.1 g (69% of theory) of the title compound.

$^1$H NMR (400 MHz, DMSO-$d_6$): δ [ppm]=1.40-1.55 (m, 2H), 1.58-1.77 (m, 2H), 1.78-2.02 (m, 4H), 2.15 (s, 3H), 2.17-2.30 (m, 1H), 7.27 (d, 1H), 7.32 (d, 1H), 7.42-7.51 (m, 3H), 7.58-7.66 (m, 2H), 8.29 (s, 1H), 10.90 (s, 1H).

LC-MS (Method 1): $R_t$=1.32 min; MS (ESIpos): m/z=436 [M+H]$^+$.

V.1-c (5r,8r)-3-(4'-Chloro-4-methylbiphenyl-3-yl)-4,8-dihydroxy-8-(trifluoromethyl)-1-azaspiro[4.5]dec-3-en-2-one

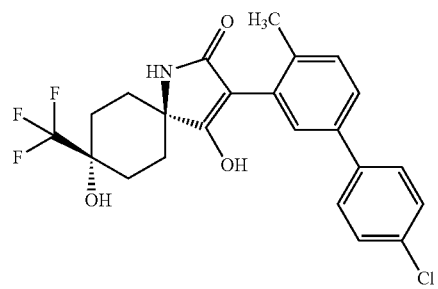 [SMILES: Cc1ccc(-c2ccc(Cl)cc2)cc1C1=C(O)[C@]2(CC[C@](O)(C(F)(F)F)CC2)NC1=O]

Under argon, 24 mg (0.030 mmol) of dichloro[1,1'-bis(diphenylphosphino)ferrocene]palladium/dichloromethane complex were added to 125 mg (0.30 mmol) of (5r,8r)-3-(5-bromo-2-methylphenyl)-4,8-dihydroxy-8-(trifluoromethyl)-1-azaspiro[4.5]dec-3-en-2-one (Example 40A) in 13 ml of degassed 1,2-dimethoxyethane. The mixture was stirred at room temperature for 5 minutes, and 70 mg (0.45 mmol) of (4-chlorophenyl)boronic acid and a solution of 339 mg (1.04 mmol) of caesium carbonate in 815 µl of degassed water was then added. The reaction mixture was heated in a closed vessel under microwave irradiation at 150° C. for 10 minutes. After cooling, 100 µl of concentrated aqueous hydrogen chloride solution were added to the reaction, and the mixture was concentrated under reduced pressure. The residue was taken up in dichloromethane and washed with aqueous 5% strength citric acid (pH=4.0-4.5) and water. The organic phase was dried over sodium sulphate and concentrated by evaporation. The crude product was purified by chromatography on silica gel (mobile phase: hexane/ethyl acetate gradient) and by HPLC chromatography (C18 phase, mobile phase: water/acetonitrile gradient/0.1% formic acid), giving 17.4 mg (13% of theory) of the title compound.

$^1$H NMR (400 MHz, methanol-$d_4$): δ [ppm]=1.41-1.53 (m, 2H), 1.85-2.01 (m, 4H), 2.24 (s, 3H), 2.33-2.46 (m, 2H), 7.32 (d, 1H), 7.35-7.42 (m, 3H), 7.46 (dd, 1H), 7.58 ("d", 2H).

LC-MS (Method 1): $R_t$=1.19 min; MS (ESIpos): m/z=452 [M+H]$^+$.

For Working Example 1-2

V.2-a (=Compound of Table 2, Row 10, p. 45 of WO10/063378)

(5r,8r)-3-(4'-Chloro-3'-fluoro-4-methylbiphenyl-3-yl)-4-hydroxy-8-methoxy-8-methyl-1-azaspiro[4.5]dec-3-en-2-one

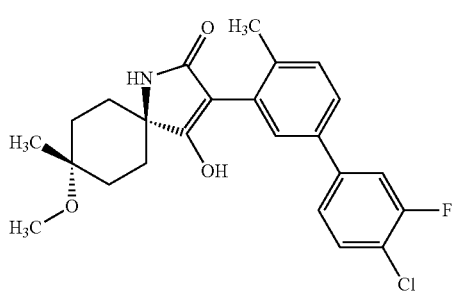 [SMILES: CO[C@]1(C)CC[C@]2(CC1)NC(=O)C(c1cc(-c3ccc(Cl)c(F)c3)ccc1C)=C2O]

Under nitrogen 6.22 g (55.4 mmol) of potassium tert-butoxide were added to 23.5 g (50.4 mmol) of the compound from Example 28A in 250 ml of N,N-dimethylformamide. The reaction mixture was stirred at room temperature for 15 minutes. The mixture was then concentrated, the residue was taken up in water and acidified with 1N aqueous hydrogen chloride solution, the mixture was stirred for 30 minutes and filtered off with suction and the precipitate was washed with water and dried. This gave 21.4 g (about 90% pure, 89% of theory) of the title compound.

$^1$H NMR (300 MHz, DMSO-$d_6$): δ [ppm]=1.08 (s, 3H), 1.10-1.22 (m, 2H), 1.56-1.81 (m, 4H), 1.99-2.14 (m, 2H), 2.19 (s, 3H), 3.10 (s, 3H), 7.29 (d, 1H), 7.40 (d, 1H), 7.46-7.56 (m, 2H), 7.60-7.72 (m, 2H), 8.05 (s, 1H), 10.86 (s, 1H).

LC-MS (Method 1): $R_t$=1.25 min; MS (ESIpos): m/z=430 [M+H]$^+$.

V.2-b (5s,8s)-3-(4'-Chloro-3'-fluoro-4-methylbiphenyl-3-yl)-4-hydroxy-8-(trifluoromethyl)-1-azaspiro[4.5]dec-3-en-2-one

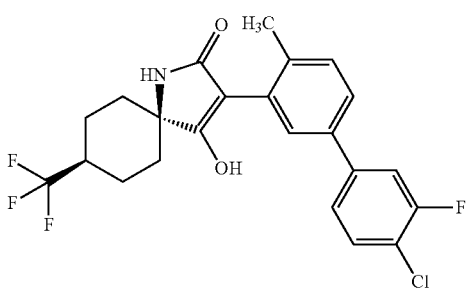 [SMILES: Cc1ccc(-c2ccc(Cl)c(F)c2)cc1C1=C(O)[C@]2(CC[C@H](C(F)(F)F)CC2)NC1=O]

Under argon, 1.01 g (1.24 mmol) of dichloro[1,1'-bis(diphenylphosphino)ferrocene]palladium/dichloromethane complex were added to 5.00 g (12.4 mmol) of the compound from Example 37A in 500 ml of degassed 1,2-dimethoxyethane. The mixture was stirred at room temperature for 5 minutes, and 3.24 g (18.5 mmol) of (4-chloro-3-fluorophenyl)boronic acid and a solution of 14.1 g (43.3 mmol) of caesium carbonate in 30 ml of degassed water was then added. The reaction mixture was heated under reflux for 2 h. After cooling, 10 ml of concentrated aqueous hydrogen chloride solution were added, the aqueous phase was separated off, magnesium sulphate was added, the mixture was filtered through silica gel, the filter cake was washed with ethyl acetate and the mixture was concentrated. Purification of the crude product by chromatography on silica gel (mobile phase: hexane/ethyl acetate gradient) and crystallization from ethyl acetate gave 2.48 g (44% of theory) of the title compound.

$^1$H NMR (300 MHz, DMSO-$d_6$): δ [ppm]=1.45-1.57 (m, 2H), 1.62-1.79 (m, 2H), 1.81-2.05 (m, 4H), 2.19 (s, 3H), 2.20-2.33 (m, 1H), 7.32 (d, 1H), 7.41 (d, 1H), 7.49-7.58 (m, 2H), 7.64 (t, 1H), 7.70 (dd, 1H), 8.33 (s, 1H), 10.95 (s, 1H).

LC-MS (Method 1): $R_t$=1.34 min; MS (ESIpos): m/z=454 [M+H]$^+$.

V.2-c (5r,8r)-3-(4'-Chloro-3'-fluoro-4-methylbiphenyl-3-yl)-4,8-dihydroxy-8-(trifluoromethyl)-1-azaspiro[4.5]dec-3-en-2-one

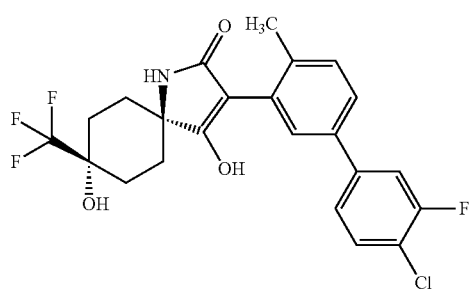 [SMILES: Cc1ccc(-c2ccc(Cl)c(F)c2)cc1C1=C(O)[C@]2(CC[C@](O)(C(F)(F)F)CC2)NC1=O]

Under argon, 24 mg (0.030 mmol) of dichloro[1,1'-bis(diphenylphosphino)ferrocene]palladium/dichloromethane complex were added to 125 mg (0.30 mmol) of (5r,8r)-3-(5-bromo-2-methylphenyl)-4,8-dihydroxy-8-(trifluoromethyl)-1-azaspiro[4.5]dec-3-en-2-one (Example 40A) in 13 ml of degassed 1,2-dimethoxyethane. The mixture was stirred at room temperature for 5 minutes, and 78 mg (0.45 mmol) of (4-chloro-3-fluorophenyl)boronic acid and a solution of 340 mg (1.04 mmol) of caesium carbonate in 815 μl of degassed water was then added. The reaction mixture was heated in a closed vessel under microwave irradiation at 150° C. for 10 minutes. After cooling, 100 μl of concentrated aqueous hydrogen chloride solution were added to the reaction, and the mixture was concentrated under reduced pressure. The residue was taken up in dichloromethane and washed with aqueous 5% strength citric acid (pH=4.0-4.5) and water. The organic phase was dried over sodium sulphate and concentrated by evaporation. The crude product was purified by chromatography on silica gel (mobile phase: hexane/ethyl acetate gradient), giving 68 mg (49% of theory) of the title compound.

$^1$H NMR (300 MHz, methanol-$d_4$): δ [ppm]=1.41-1.56 (m, 2H), 1.85-1.99 (m, 4H), 2.25 (s, 3H), 2.32-2.48 (m, 2H), 7.10-7.25 (m, 1H), 7.34 (d, 1H), 7.40 (dd, 1H), 7.43-7.56 (m, 3H).

LC-MS (Method 1): $R_t$=1.19 min; MS (ESIpos): m/z=470 [M+H]$^+$.

For Working Example 1-3

V.3-a (=V.1-a)=Compound of Table 1, Row 20, p. 40 of WO10/063378

V.3-b (5s,8s)-3-(4'-Chloro-4-methylbiphenyl-3-yl)-4-hydroxy-8-(methoxymethyl)-1-azaspiro[4.5]dec-3-en-2-one

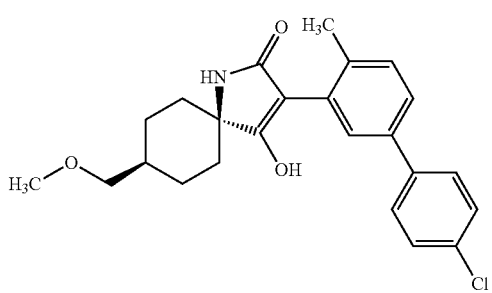 [SMILES: COC[C@H]1CC[C@]2(CC1)NC(=O)C(c1cc(-c3ccc(Cl)cc3)ccc1C)=C2O]

5.26 g (46.9 mmol) of potassium tert-butoxide were added to 10.4 g (23.4 mmol) of the compound from Example 30A in 35 ml of N,N-dimethylformamide. The reaction mixture was heated at 80° C. for 15 minutes. After cooling, the mixture was concentrated, the residue was taken up in water and the solution was added dropwise to 2N aqueous hydrogen chloride solution. The precipitate was filtered off with suction, washed with water and dried. This gave 9.3 g of the title compound.

$^1$H NMR (300 MHz, DMSO-d$_6$): δ [ppm]=1.21-1.47 (m, 4H), 1.48-1.64 (m, 1H), 1.65-1.78 (m, 2H), 1.81-1.97 (m, 2H), 2.18 (s, 3H), 3.16 (d, 2H), 3.24 (s, 3H), 7.30 (d, 1H), 7.34 (d, 1H), 7.44-7.53 (m, 3H), 7.61-7.68 (m, 2H), 8.13 (s, 1H), 10.77 (s, 1H).

LC-MS (Method 3): R$_t$=1.25 min; MS (ESIpos): m/z=412 [M+H]$^+$.

The substance was disclosed as isomer mixture as Example I-1-a-5 of WO 07/048545.

For Working Example 1-4

V.4-a (=V.2-a)=Compound of Table 2, Row 10, p. 45 of WO10/063378

V.4-b (5s,8s)-3-(4'-Chloro-3'-fluoro-4-methylbiphenyl-3-yl)-4-hydroxy-8-(methoxymethyl)-1-azaspiro[4.5]dec-3-en-2-one

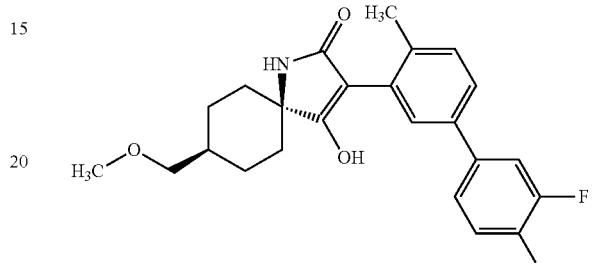

Under argon, 1.10 g (6.31 mmol) of (4-chloro-3-fluorophenyl)boronic acid and a solution of 6.00 g (18.4 mmol) of caesium carbonate in 13 ml of degassed water was added to 2.00 g (5.26 mmol) of the compound from Example 41A and 215 mg (0.26 mmol) of dichloro[1,1'-bis(diphenylphosphino)ferrocene]palladium/dichloromethane complex in 213 ml of degassed 1,2-dimethoxyethane. The reaction mixture was heated under reflux for 2 h. After cooling, 2.5 ml of concentrated aqueous hydrogen chloride solution and sodium sulphate were added, the mixture was filtered through silica gel and sodium sulphate, the filter cake was washed with ethyl acetate and the filtrate was concentrated. The crude product was purified by chromatography on silica gel (mobile phase: hexane/ethyl acetate gradient). The product was then stirred with aqueous sodium bicarbonate solution, acidified with concentrated aqueous hydrogen chloride solution, filtered off with suction, washed with water and dried. This gave 1.50 g (65% of theory) of the title compound.

$^1$H NMR (300 MHz, DMSO-d$_6$): δ [ppm]=1.21-1.47 (m, 4H), 1.48-1.64 (m, 1H), 1.65-1.78 (m, 2H), 1.81-1.97 (m, 2H), 2.19 (s, 3H), 3.16 (d, 2H), 3.24 (s, 3H), 7.31 (d, 1H), 7.40 (d, 1H), 7.48-7.57 (m, 2H), 7.60-7.74 (m, 2H), 8.13 (s, 1H), 10.79 (s, 1H).

LC-MS (Method 1): R$_t$=1.26 min; MS (ESIpos): m/z=430 [M+H]$^+$.

Table V gives an overview of the comparative examples which the applicant considers to be the closest prior art

TABLE V

| Ex. | Structure/Name | Disclosed in |
|---|---|---|
| V.1-a | (structure) | Table 1, row 20, p. 40 of WO10/063378 |

TABLE V-continued

| Ex. | Structure/Name | Disclosed in |
|---|---|---|
| V.1-b | | |
| V.1-c | | |
| V.2-a | | Table 2, row 10, p. 45 of WO10/063378 |
| V.2-b | | |
| V.2-c | | |

TABLE V-continued

| Ex. | Structure/Name | Disclosed in |
| --- | --- | --- |
| V.3-a | | Table 1, row 20, p. 40 of WO10/063378 |
| V.3-b | | |
| V.4-a | | Table 2, row 10, p. 45 of WO10/063378 |
| V.4-b | | |

WORKING EXAMPLES

Example 1-1

(5r,8r)-3-(4'-Chloro-4-methylbiphenyl-3-yl)-4-hydroxy-8-methoxy-8-(trifluoromethyl)-1-azaspiro[4.5]dec-3-en-2-one

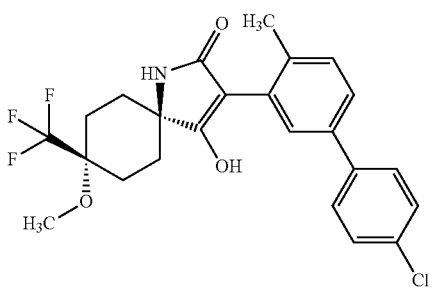 [SMILES: CO[C@]1(C(F)(F)F)CC[C@]2(CC1)NC(=O)C(c1cc(-c3ccc(Cl)cc3)ccc1C)=C2O]

3.07 g (27.31 mmol) of potassium tert-butoxide were added to 6.80 g (13.66 mmol) of methyl 1-{[(4'-chloro-4-methylbiphenyl-3-yl)acetyl]amino}-4-methoxy-4-(trifluoromethyl)cyclohexanecarboxylate (Example 32A) in 68 ml of N,N-dimethylformamide. The reaction mixture was stirred at 80° C. for 60 minutes. For work-up, the cold reaction mixture was poured into 1500 ml of ice-water and acidified with aqueous hydrochloric acid. The crude product was filtered off, dried and pre-purified by chromatography (column: Chiralpak IA 5 μm, 250×30 mm; hexane/ethanol gradient in the presence of 0.1% formic acid). Concentration by evaporation and crystallization from diethyl ether gave 3.57 g (56% of theory) of the title compound.

$^1$H NMR (300 MHz, DMSO-d$_6$): δ [ppm]=1.25-1.41 (m, 2H), 1.83-1.99 (m, 4H), 2.00-2.14 (m, 2H), 2.15 (s, 3H), 3.34 (s, 3H), 7.28 (d, 1H), 7.32 (d, 1H), 7.42-7.51 (m, 3H), 7.58-7.67 (m, 2H), 8.41 (s, 1H), 10.98 (s, 1H).

LC-MS (Method 1): R$_t$=1.31 min; MS (ESIpos): m/z=466 [M+H]$^+$.

Example 1-2

(5r,8r)-3-(4'-Chloro-3'-fluoro-4-methylbiphenyl-3-yl)-4-hydroxy-8-methoxy-8-(trifluoromethyl)-1-azaspiro[4.5]dec-3-en-2-one

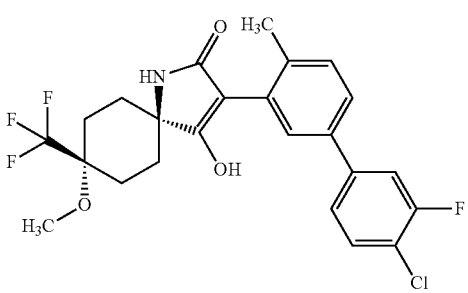 [SMILES: CO[C@]1(C(F)(F)F)CC[C@]2(CC1)NC(=O)C(c1cc(-c3ccc(Cl)c(F)c3)ccc1C)=C2O]

Under argon, 67.70 mg (0.083 mmol) of dichloro[1,1'-bis(diphenylphosphino)ferrocene]palladium/dichloromethane complex were added to 300.00 mg (0.69 mmol) of 3-(5-bromo-2-methylphenyl)-4-hydroxy-8-methoxy-8-(trifluoromethyl)-1-azaspiro[4.5]dec-3-en-2-one (Example 42A) in 28 ml of degassed 1,2-dimethoxyethane. The mixture was stirred at room temperature for 5 minutes, and 216.83 mg (1.24 mmol) of (4-chloro-3-fluorophenyl)boronic acid and a solution of 945.40 mg (2.90 mmol) of caesium carbonate in 1 ml of degassed water was then added. The reaction mixture was heated in a microwave at 150° C. for 40 min. After cooling, 0.4 ml of concentrated aqueous hydrogen chloride solution was added, the mixture was filtered, the precipitate was washed with dichloromethane and with methanol and the combined organic phases were concentrated under reduced pressure. The crude product was pre-purified by chromatography on silica gel (mobile phase: hexane/ethyl acetate gradient). Final purification was by RP chromatography (mobile phase: water/formic acid/acetonitrile gradient). This gave 43 mg (13% of theory) of the title compound.

$^1$H NMR (400 MHz, DMSO-d$_6$): δ [ppm]=1.27-1.39 (m, 2H), 1.85-1.99 (m, 4H), 2.00-2.13 (m, 2H), 2.16 (s, 3H), 3.34 (s, 3H), 7.29 (d, 1H), 7.38 (d, 1H), 7.45-7.54 (m, 2H), 7.57-7.70 (m, 2H), 8.36 (s, 1H), 10.97 (s, 1H).

LC-MS (Method 1): R$_t$=1.34 min; MS (ESIpos): m/z=484 [M+H]$^+$.

Alternatively, the target structure could be prepared as follows:

15.22 g (135.68 mmol) of potassium tert-butoxide were added to 35.00 g (67.84 mmol) of methyl 1-{[(4'-chloro-3'-fluoro-4-methylbiphenyl-3-yl)acetyl]amino}-4-methoxy-4-(trifluoromethyl)cyclohexanecarboxylate (Example 33A) in 350 ml of N,N-dimethylformamide. The reaction mixture was stirred at room temperature for 30 minutes. For work-up, the cold reaction mixture was poured into 8000 ml of ice-water and acidified with aqueous hydrochloric acid. The crude product was filtered off, dried and pre-purified by silica gel chromatography (dichloromethane/ethyl acetate gradient). The solid obtained was crystallized from diethyl ether. This gave 9.33 g (28% of theory) of the title compound.

Example 1-3

(5r,8r)-3-(4'-Chloro-4-methylbiphenyl-3-yl)-4-hydroxy-8-methoxy-8-(methoxymethyl)-1-azaspiro[4.5]dec-3-en-2-one

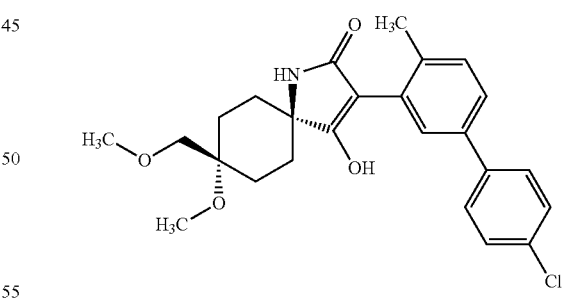

Under nitrogen 148 mg (1.32 mmol) of potassium tert-butoxide were added to 570 mg (1.20 mmol) of the compound from Example 35A in 5 ml of N,N-dimethylformamide. The reaction mixture was stirred at room temperature for 15 minutes. The mixture was then concentrated, the residue was taken up in ice-water and acidified with 1N aqueous hydrogen chloride solution, the mixture was stirred for 30 minutes and filtered off with suction and the precipitate was washed with water and dried. By two preparative HPLC [1. column: Chromatorex C18, 10 μm, 125 mm×30 mm; mobile phase: water/acetonitrile gradient with addition of 0.1% formic acid; 2.

column: Chiralpak IC, 5 µm, 250 mm×20 mm; mobile phase: hexane/ethanol=80/20 with addition of 0.1% formic acid; flow rate: 25 ml/min; temperature: RT], the diastereomers were separated. This gave 105 mg (20% of theory) of the title compound.

$^1$H NMR (300 MHz, DMSO-$d_6$): δ [ppm]=1.12-1.27 (m, 2H), 1.48-1.65 (m, 2H), 1.75-1.88 (m, 2H), 1.99-2.14 (m, 2H), 2.18 (s, 3H), 3.15 (s, 3H), 3.28 (m, 5H), 7.30 (d, 1H), 7.34 (d, 1H), 7.44-7.54 (m, 3H), 7.61-7.69 (m, 2H), 8.10 (s, 1H), 10.83 (s, 1H).

LC-MS (Method 2): $R_t$=1.19 min; MS (ESIpos): m/z=442 [M+H]$^+$.

Example 1-4

(5r,8r)-3-(4'-Chloro-3'-fluoro-4-methylbiphenyl-3-yl)-4-hydroxy-8-methoxy-8-(methoxymethyl)-1-azaspiro[4.5]dec-3-en-2-one

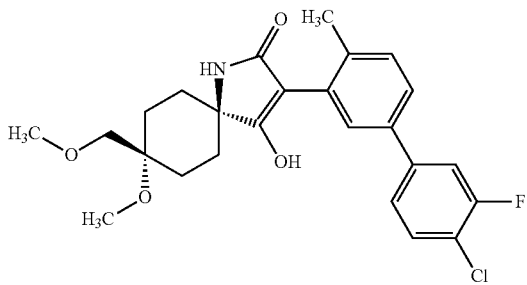 [SMILES: COC[C@]1(OC)CC[C@@]2(CC1)NC(=O)C(c1cc(-c3ccc(Cl)c(F)c3)ccc1C)=C2O]

Under nitrogen 1.64 g (14.7 mmol) of potassium tert-butoxide were added to 6.55 g (13.3 mmol) of the compound from Example 34A in 60 ml of N,N-dimethylformamide. The reaction mixture was stirred at room temperature for 15 minutes. The reaction mixture was then added to ice-water, 1N aqueous hydrogen chloride solution was added dropwise until a pH of 1-2 had been reached, the mixture was stirred for 30 minutes and filtered off with suction, the filter cake was washed with water and the precipitate was dried. For further purification, the product was dissolved in 1N aqueous sodium hydroxide solution, precipitated by acidification with aqueous 1 N hydrochloric acid, stirred for 30 minutes, washed with water, filtered off and dried. This gave 6.00 g (98% of theory) of the title compound.

$^1$H NMR (300 MHz, DMSO-$d_6$): δ [ppm]=1.12-1.26 (m, 2H), 1.50-1.65 (m, 2H), 1.76-1.89 (m, 2H), 1.98-2.15 (m, 2H), 2.19 (s, 3H), 3.15 (s, 3H), 3.28 (s, 5H), 7.31 (d, 1H), 7.39 (d, 1H), 7.49-7.57 (m, 2H), 7.64 (t, 1H), 7.69 (dd, 1H), 8.14 (s, 1H), 10.82 (s, 1H).

LC-MS (Method 2): $R_t$=1.21 min; MS (ESIpos): m/z=460 [M+H]$^+$.

3. ASSAYS 3.1 Human ACC Enzyme Assays

The ACC1 and ACC2 inhibition data were obtained using the two assays described below. In most cases, a common serial dilution series of the test substances was prepared for the two measurements, and several substance plate copies were then made from this dilution series using a 384-well 50-nl capillary pipettor (Hummingbird™ from Genomics Solutions). These were then in each case used in the ACC1 and the ACC2 assay such that, for optimum comparability, the two enzyme inhibition measurements were carried out using copies of the same substance dilution series.

Human ACC1 Enzyme Assay

The hACC1-inhibitory activity of the substances of this invention was measured using the hACC1 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was C-terminally FLAG-tagged recombinant human ACC1 (acetyl-coenzyme A carboxylase alpha transcript variant 1) (GenBank Accession No. NM_198834), (amino acids 39-end), expressed in baculovirus-infected insect cells (Hi5) and purified by anti-FLAG affinity chromatography.

For the assay, 50 nl of a 100-times concentrated solution of the test substance in DMSO were pipetted into a white low-volume 384-well microtitre plate (Greiner Bio-One, Frickenhausen, Germany), 2.5 µl of a solution of hACC1 in assay buffer [50 mM HEPES/NaOH pH 7.5, 2 mM MgCl$_2$, 2 mM potassium citrate, 12 mM NaHCO$_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 µl of a solution of adenosine triphosphate (ATP, 100 µM=>final concentration in 5 µl of assay volume: 50 µM) and acetyl-CoA (20 µM=>final concentration in 5 µl assay volume: 10 µM) in assay buffer, and the resulting mixture was incubated at 22° C. for the reaction time of 45 min. The concentration of the hACC1 was adjusted to the respective activity of the enzyme and set such that the assay was carried out in the linear range. Typical concentrations were in the range of 1.75 µl. The reaction was stopped by addition of 2.5 µl of the "ADP-GLO reagent" (1:1.5-times diluted), and the resulting mixture was incubated at 22° C. for 1 h to convert the unreacted ATP completely into cAMP. 2.5 µl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC1. The data were normalized (enzyme reaction without inhibitor=0% inhibition, all other assay components but no enzyme=100% inhibition). Usually, the test substances were tested on the same microtitre plates at 10 different concentrations in the range from 20 µM to 1 nM (20 µM, 6.7 µM, 2.2 µM, 0.74 µM, 0.25 µM, 82 nM, 27 nM, 9.2 nM, 3.1 nM and 1 nM, the dilution series were prepared before the assay based on the 100-times concentrated solution by serial 1:3 dilutions) in two replications for each concentration, and the IC$_{50}$ values were calculated with a 4-parameter fit using an inhouse software.

Human ACC2 Enzyme Assay

The hACC2-inhibitory activity of the substances of this invention was measured using the hACC2 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was C-terminally FLAG-tagged recombinant human ACC2 (acetyl-coenzyme A carboxylase 2, GenBank Accession No. NP_001084), (amino acids 27-end), expressed in baculovirus-infected insect cells (Hi5) and purified by anti-FLAG affinity chromatography. For the assay, 50 nl of a 100-times concentrated solution of the test substance in DMSO were pipetted into a white low-volume 384-well microtitre plate (Greiner Bio-One, Frickenhausen, Germany), 2.5 µl of a solution of hACC2 in assay buffer [50 mM HEPES/NaOH pH 7.5, 2 mM MgCl$_2$, 2 mM potassium citrate, 12 mM NaHCO$_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 µl of a solution of adenosine triphosphate (ATP, 100 µM=>final concentration in 5 µl of assay volume: 50 µM) and acetyl-CoA (20 µM=>final concentration in 5 µl assay volume: 10 µM) in assay buffer, and the resulting mixture was incubated at 22° C. for the reaction time of 45 min. The concentration of the hACC2 was adjusted to the respective activity of the enzyme and set such that the assay was carried out in the linear range. Typical concentrations were in the range of 2 ng/µl. The reaction was stopped by addition of 2.5 µl of the "ADP-GLO reagent" (1:1.5-times diluted), and the resulting mixture was incubated at 22° C. for 1 h to convert the unreacted ATP completely into cAMP. 2.5 µl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC2. The data were normalized (enzyme reaction without inhibitor=0% inhibition, all other assay components but no enzyme=100% inhibition). Usually, the test substances were tested on the same microtitre plates at 10 different concentrations in the range from 20 µM to 1 nM (20 µM, 6.7 µM, 2.2 µM, 0.74 µM, 0.25 µM, 82 nM, 27 nM, 9.2 nM, 3.1 nM and 1 nM, the dilution series were prepared before the assay based on the 100-times concentrated solution by serial 1:3 dilutions) in two replications for each concentration, and the IC$_{50}$ values were calculated with a 4-parameter fit using an inhouse software.

3.2 Cell Assays

In accordance with the invention, the substances were tested in cell-based assays for the ability of the substances of inhibiting tumour cell proliferation after a 96-hour incubation with the substance. Cell viability was tested using the Cell-Titer-Glo® luminescent cell viability assay (Promega). The cells were sown at a density of 2000-5000 cells/well (depending on the cell line) in 100 µl growth medium on 96-well microtitre plates. For each cell line examined, cells were sown on a separate plate to determine the luminescence at t=0 hours and t=96 hours. After overnight incubation at 37° C., the luminescence values for the t=0 samples were determined. The dose plates for the t=96 hours points in time were treated with substances diluted with growth medium. The cells were then incubated at 37° C. for 96 hours, and the luminescence values for the t=96 hours samples were then determined. For data analysis, the t=0 values were subtracted from the t=96 hours values for treated and untreated samples. The differences in luminescence in percent between substance-treated samples and control values were used to determine the growth inhibition in percent.

The substances were tested in the following cell lines which represent the stated indications in an exemplary manner:

| Cell line | Source | Indication |
|---|---|---|
| MCF7 | ATCC | hormone receptor-positive breast carcinoma |
| KM12 | NCI | colorectal carcinoma |
| PC3 | DMSZ | androgen receptor-negative prostate carcinoma |
| H460 | ATCC | non-small-cell bronchial carcinoma |

ATCC: American Type Culture Collection
NCI: National Cancer Institute
DMSZ: Deutsche Sammlung von Mikroorganismen and Zellkulturen GmbH 3.3 Analysis of the ACC1 Expression in Tumour Tissue and Normal Tissue The ACC1 expression was determined using a microarray. To this end, the RNA of various tumour tissues and the corresponding normal tissues was isolated. The method made use of Trizol RNA extraction reagent (Invitrogen) and subsequent purification using the RNeasy mini kit (Qiagen). Moreover, a DNase I (Qiagen) digestion was carried out to eliminate genomic DNA. For quality control, the total RNA was analyzed with the aid of an RNA LabChip on an Agilent Bioanalyzer 2100 Platform (Agilent Technologies), and the RNA concentration was determined using the Peqlab Nano-Drop system. For hybridization, the one-cycle eukaryotic target labeling assay from Affymetrix was used, and the array was then read on an AffymetrixGeneChip 3000 scanner (Affymetrix). Evaluation and quality control were carried out using the Expressionist Pro 4.0 Refiner (GeneData) software.

3.4 Assays for Determining the Octanol/Water Distribution Coefficient (logP/D) Membrane Affinity (logMA) and Protein Binding to Human Serum Albumin (K$_d$ HSA)

Assay for Determining the Octanol/Water Distribution Coefficient (logP/D):

The distribution coefficient octanol/water P or D is a key parameter for estimating membrane penetration and permeability. It is defined as the ratio of the equilibrium concentrations of a substance in the two-phase system octanol/water.

$$P/D = \frac{c_{octanol}}{c_{water}}$$

P=partition
D=distribution
c(octanol)=concentration of the substance in the octanol phase
c(water)=concentration of the substance in the aqueous phase It is usually stated in form of the decadic logarithm (logP or logD).

logP describes the distribution behaviour of a substance exclusively present in its neutral form. logD describes the distribution behaviour of a substance at a certain pH; depending on the ionisation constant pKa of the substance, some of the substance may be present in ionic form, and some in neutral form.

The logP/D of the active compounds was determined using an isocratic HPLC method (HPLC=high performance liquid chromatography) (literature: OECD Guideline for Testing of Chemicals No. 117). The method is based on the correlation of the HPLC retention time of the test substance to that of reference substances with known distribution coefficients.

The test substance was employed as a 10 mM solution in DMSO (DMSO=dimethyl sulphoxide). 10 µl of this solution were made up to 100 µl with a methanol/water mixture in a ratio of 7+3.

The nine reference substances were dissolved individually in methanol. The concentration is shown in Table 1. 100 µl each of the stock solutions were added to an HPLC vial and mixed with 300 µl of water.

TABLE 1

| Reference substance | log P | Approximate retention time [min] | Molar mass | Stock sol. weighed in [mg/10 ml] |
|---|---|---|---|---|
| acetanilide | 1.0 | 0.8 | 135.2 | 12 |
| 4-methylbenzyl alcohol | 1.6 | 0.9 | 122.2 | 15 |
| methyl benzoate | 2.1 | 1.1 | 136.2 | 18 |
| ethyl benzoate | 2.6 | 1.4 | 150.2 | 19 |
| naphthalene | 3.6 | 2.1 | 128.2 | 3 |
| 1,2,4-trichlorobenzene | 4.2 | 3.4 | 181.5 | 14 |
| 2,6-diphenylpyridine | 4.9 | 4.6 | 231.3 | 5 |
| triphenylamine | 5.7 | 8.0 | 245.3 | 8 |
| DDT | 6.2 | 10.3 | 354.5 | 10 |

A formamide solution was used to determine the hold-up time. To this end, 7 mg of formamide were dissolved in 10 ml of methanol. 100 µl of this stock solution were mixed with 500 µl of methanol and 200 µl of water.

All solutions were chromatographed using a flow rate of 1.00 ml/min.

Chromatographic Conditions:

| HPLC system | Waters Alliance HT 2790 |
|---|---|
| UV detector | DAD Waters 996 |
| MS detector | MS Micromass ZQ |
| HPLC software | MassLynx 4.1 from Waters |
| Column | Spherisorb ODS 3 µm 4.6 × 60 mm |
| Mobile phase | methanol + water with 0.01M ammonium acetate (0.77 g/liter) 75 + 25, pH 7.0 |

Injection Volumes:

| formamide | 5 µl |
|---|---|
| references | 5 µl |
| test substance | 15 µl |

Injection Protocol:
formamide, references, test substance 1, test substance 2, . . . , formamide, references.

Evaluation of the retention times was carried out in a diode array detector (DAD) at 200-400 nm Via the molecular mass, the identity of the test substance was checked using the downstream mass spectrometer.

The HPLC run was evaluated using the Waters software Masslynx 4.1.

The logP/D values were calculated using the software "POW Determination" (proprietary development).

Assays for Determining Membrane Affinity logMA and Protein Binding to Human Serum Albumin (HSA):

Determination of membrane affinity and protein binding to human serum albumin (HSA) was carried out via Transil technology (literature: A. Loidl-Stahlhofen, A. Eckert, T. Hartmann, M. Schöttner J Pharm Sci 90, 599-606 (2001)). Transil® (commercially available from Sovicell in Leipzig, Germany) are glass beads (diameter 10-12 µm) coated with a double-layer membrane of phosphatidylcholine (MA-Transil) or covalently attached human serum albumin (HSA-Transil).

To determine the logMA and the protein binding constant to HSA, the commercially available TRANSIL Intestinal Absorption & HSA Binding Combined Assay Kit was used. This is a 96-well microtitre plate (96 well-MTP) which is filled with Transil and can be used to determine MA-Transil and HSA-Transil binding of in each case eight active compounds. For each active compound, the Transil plate provides a row of 12 wells. Two wells serve as reference and are only filled with buffer pH 7.4. Five further wells contain MA-Transil in various increasing concentrations, the five remaining wells contain HSA-Transil in various increasing concentrations.

To determine binding of an active compound to Transil, the supernatant of the wells with Transil was quantified against the reference solution without Transil via HPLC-MS coupling (HPLC-MS=high performance liquid chromatography/ mass spectrometry).

This is how the individual steps of the assay were carried out:

From the internal substance store, the active compounds were delivered in a 96-well MTP. This plate is referred to as mother plate. Each well contained 30 µl of a 10 mmol solution of active compound in DMSO (dimethyl sulphoxide). Two wells at the start (well A1) and at the end of the plate (well H12) were filled with 30 µl of a 10 mmol solution of warfarin in DMSO. Warfarin, whose membrane affinity and binding to HSA is known, serves to check whether the measurement is correct. The mother plate was used to prepare a daughter plate with a 1 to 4000 dilution with a mixture of buffer pH 7.4 and DMSO in a ratio of 1+1. The active compound concentration of each well was 2.5 µmol/liter, the volume of each well was 400 µl.

Using a Hamilton pipetting robot Microlab STAR, the 96 active compounds from the daughter plate were divided onto 12 Transil plates in total. From each well of the daughter plate, 12 times 20 µl were removed. The concentration of each well of the Transil plate was 0.25 µmol/liter, which corresponds to a dilution of 1 to 10. The DMSO content was 5%.

The filled Transil plates were each resuspended for two minutes, then allowed to stand at room temperature for at least two minutes and then centrifuged at 600 rotations per minute for five minutes. The pipetting robot was then used to remove 20 µl of supernatant from each well of the Transil plate and to transfer these to a separate microtitre plate. Here, the supernatants of in each case four Transil plates were pooled in a microtitre plate, so that at the end there were three pooled microtitre plates with in each case 80 µl of solution and an active compound concentration of 62.5 nM per well.

Prior to quantification of the active compounds by HPLC-MS, an optimization has to be carried out for each active compound where by way of a single injection daughter ion and optimum electrical voltages are determined. To this end, the pipetting robot prepared a dilution of the mother plate of 1 to 10 000 000 in an acetonitrile/water mixture in a ratio of 8+2 in a separate microtitre plate. This microtitre plate was measured by HPLC-MS using the software Discovery Quant Optimize from AB Sciex. The three pooled microtitre plates were measured by HPLC-MS using the software Discovery Quant Analyze from AB Sciex.

Chromatographic Conditions:
HPLC-MS system: Agilent 1200 Rapid resolution HPLC
Sciex Triple Quad 5500 mass spectrometer (from AB Sciex)
PAL Autosampler DLW Option
Software: Analyst 1.4 (from AB Sciex)
Discovery Quant Optimize (from AB Sciex)
Discovery Quant Analyze (from AB Sciex)
Optimization:
Column: capillary
Injection volume: 5 µl
Flow rate: 0 min->80 µl/min
0-0.19 min->80 µl/min
0.20-0.65 min->30 µl/min
0.66-0.7 min->150 µl/min
Mobile phase: A=acetonitrile+0.05% formic acid
B=water+0.05% formic acid
isocratic A:B 8+2
Analysis:
Column: Poroshell 120 SB-C18 2.7 µm 3×30 mm
Injection volume: 2 µl
Flow rate: 1 ml/min:
Mobile phase: gradient
A=acetonitrile+0.05% formic acid
B=water+0.05% formic acid
0 min->95% A, 5% B
0-1.0 min->5% A, 95% B increasing in a linear manner
1.0-2.2 min->5% A, 95% B isocratic
2.21-2.3 min->95% A, 5% B isocratic 3.5 Determination of Plasma Protein Binding by Equilibrium Dialysis The binding of test substances to plasma proteins is determined by equilibrium dialysis by means of the Ht-dialysis apparatus (96-well) made of Teflon and a semipermeable membrane (regenerated cellulose, MWCO 12-14K). This separates 150 µl each of a plasma side and a buffer side (50 mM phosphate buffer). The test substance is added in 2 concentrations (usually 3 and 0.3 µM) to the plasma side and binds to plasma proteins. The unbound fraction of the test substance passes through the membrane and is distributed on either side until equilibrium is established (after approx. 6-8 h at 37° C.). The substance concentration on the buffer side and the plasma side is determined by LC-MS analysis. For this, both sides are brought by dilution with buffer or plasma to the same matrix (10% plasma) and then precipitated with methanol. The free (unbound) fraction (fu) is calculated from the quotient of the buffer and plasma concentration. Stability tests and recovery tests are run concurrently as controls. In addition, the substance in buffer is dialysed against buffer, to check the nonspecific binding to apparatus and membrane and establishment of equilibrium. Because during incubation the osmotic pressure of the plasma proteins leads to dilution of the plasma (volume shift), this possible error is determined by weighing blank plasma samples and is included in the calculation of fu. Establishment of equilibrium and plasma stability should have a value not lower than 80% and the recovery should be at least 30%. A free fraction of <1% is regarded as high, between 1 and 10% as moderate and >10% as low plasma protein binding.

3.6 Pharmacokinetic Parameters

Determination of the Pharmacokinetic Parameters of a Test Substance in the Rat and in the Dog For this, the test substances were applied in dissolved form both for intravenous, and for intragastric application, wherein compatible solubilizers such as PEG400 and/or ethanol were used in a compatible amount.

Intravenous Administration:

The test substances were applied at a dose of 0.1-1 mg/kg. Administration was as a bolus injection in the male rat and as an infusion in the female dog (15 min) At various time points after the bolus injection, and before and after the 15-minute infusion, blood samples of about 100-150 µl were removed via a catheter either from the jugular vein (rat) or from the saphenous vein (dog). Lithium-heparin was added as anticoagulant to the blood samples and they were stored in a refrigerator until required for further processing. After centrifugation of the samples for 15 min at 3000 rpm, an aliquot of 100 µl was taken from the supernatant (plasma) and was precipitated by adding 400 µl of cold ACN or methanol (absolute). The precipitated samples were frozen-out at 20° C. overnight, then centrifuged again at 3000 rpm for 15 min, before 150 µl of the clear supernatant were removed to determine the concentration. The analysis was effected by means of an Agilent 1200 HPLC system with connected LCMS/MS detection.

Calculation of the PK parameters (using PK calculation software, e.g. WinNonLin®): CLplasma: total plasma clearance of the test substance (in $1*kg/h$); CLblood: total blood clearance of the test substance (in $1*kg/h$), where ($CLblood=CLplasma*Cp/Cb$); Vss: apparent steady-state distribution volume (in 1/kg); $t½$: half-life within a specified interval (here: terminal $t½$, in h); AUCnorm: area under the plasma concentration time profile from time point zero extrapolated to infinity divided by the dose normalized for body weight (in $kg*l/h$); AUC(0-tn)norm: integrated area under the plasma concentration time profile from time point zero until the last time point at which a plasma concentration was measurable, divided by the dose normalized for body weight (in $kg*l/h$); Cmax: maximum concentration of the test substance in the plasma (in µg/l); Cmax,norm: maximum concentration of the test substance in the plasma divided by the dose normalized for body weight (in kg/l); Cb/Cp: ratio of the blood to plasma concentration distribution.

Intragastric Administration:

The test substances were administered to fasting male rats or female dogs at a dose of 0.3-1 mg/kg intragastrically as a bolus using a feeding tube. At various time points after administration, blood samples of about 100-150 µl were removed via a catheter either from the jugular vein (rat) or from the saphenous vein (dog). Lithium-heparin was added as anticoagulant to the blood samples and they were stored in a refrigerator until required for further processing. After centrifugation of the samples for 15 min at 3000 rpm, an aliquot of 100 µl was taken from the supernatant (plasma) and was precipitated by adding 400 µl of cold ACN or methanol (absolute). The precipitated samples were frozen-out at −20° C. overnight, then centrifuged at 3000 rpm for 15 min, before 150 µl of the clear supernatant were removed to determine the concentration. The analysis was effected by means of an Agilent 1200 HPLC system with connected LCMS/MS detection.

Calculation of the PK parameters (using PK calculation software, e.g. WinNonLin®):

AUCnorm: area under the plasma concentration time profile from time point zero extrapolated to infinity divided by the dose normalized for body weight (in $kg*l/h$); AUC(0-tn) norm: integrated area under the plasma concentration time profile from time point zero until the last time point at which a plasma concentration was measurable, divided by the dose normalized for body weight (in $kg*l/h$); Cmax: maximum concentration of the test substance in the plasma (in µg/l); Cmax,norm: P maximum concentration of the test substance in the plasma divided by the dose normalized for body weight (in kg/l); $t½$: half-life within a specified interval (here: terminal $t½$, in h); Fobs %: observed oral bioavailability, AUC(0- tn)norm after i.g. administration divided by AUC(0-tn)norm after i.v. administration. tmax: time point at which the maximum concentration of the test substance is measured in the plasma.

To calculate the relative bioavailability of a test substance, the AUC(0-tn)norm after i.g. administration of a suspension of a microcrystalline substance is divided by the AUC(0-tn) norm after administration of a substance solution.

3.7. In-Vivo Activity

Xenograft Model

Xenograft models in immunosuppressed mice were used to determine the antitumour activity in living organisms.

To this end, initially the maximum tolerable dose (MTD) was determined using the following protocol:

Over a period of 3 weeks, a defined dose of the test substance was administered daily orally to female nude mice (NMRI-nude (nu/nu) mice, Taconic M&B A/S), and the mice were observed daily for mortality and body weight. The MTD was defined as the highest dose which could be administered without any animal dying during the treatment phase, and without any body weight loss of more than 10% compared to the initial weight.

Xenograft models in which the test substances were administered in their MTD or, if it was not possible to determine this beforehand, in the highest dose that could be formulated in the standard vehicle, and in some cases also in lower doses were then used to determine the antitumour activity. Use was made primarily of a prostate carcinoma model with hormone-independent human PC-3 cells in male nude mice (NMRI-nude (nu/nu) mice, Taconic M&B A/S). To this end, 3 million tumour cells (suspended in medium+Matrigel 1:1, final 0.1 ml) were injected subcutaneously into the side of each animal. When the tumours extended to an area of 20-30 $mm^2$, the mice were randomized into therapy groups and therapy was initiated. The therapy was then continued until an average tumour size of 130-160 $mm^2$ had been reached in the control group, which had only been given the vehicle of the test substance, or in one of the treatment groups, with tumour area and body weight being measured 2-3 times per week. At this point in time, the experiment was terminated in all groups and the prepared tumours were weighed.

The T/C value was calculated as primary success parameter using the effect on the final tumour weight: mean tumour weight in the treatment group divided by mean of the tumour weight in the vehicle group.

4. RESULTS 4.1. Enzyme Assay

Table 2 summarizes the results of the working examples and comparative examples from the enzyme assays. For the exact determination of the selectivity, measurements of the inhibition of ACC1 and ACC2 (in each case IC50 determinations) were compared in each case pair by pair, with copies of the same substance dilution series being used in the two assays. If either the ACC1 or the ACC2 IC50 determination was not evaluated owing to an insufficient data quality, both measurements were disregarded and were not listed in the table. The selectivity of the inhibition of ACC1 vs. the inhibition of ACC2 was then determined as a mean of the selectivities observed in the individual measurements.

TABLE 2

| Example | Measurement No. | Preparation No. | ACC 1 IC50 [µmol/l] | ACC 2 IC50 [µmol/l] | Ratio IC50s ACC2/ACC1 (respective measurement) | Selectivity ACC1 vs. ACC2 (mean of the individual measurements ± standard deviation) |
|---|---|---|---|---|---|---|
| 1-1 | 1 | 1 | 0.231 | 11.5 | 50 | 49 ± 27 |
|  | 2 | 1 | 0.244 | 13.5 | 55 |  |
|  | 3 | 2 | 0.044 | 3.31 | 75 |  |
|  | 4 | 2 | 0.067 | 4.15 | 62 |  |
|  | 5 | 3 | 0.087 | 6.46 | 74 |  |
|  | 6 | 3 | 0.078 | 7.42 | 95 |  |
|  | 7 | 1 | 0.162 | 3.39 | 21 |  |
|  | 8 | 1 | 0.186 | 4.50 | 24 |  |
|  | 9 | 4 | 0.099 | 0.98 | 10 |  |
|  | 10 | 4 | 0.069 | 1.57 | 23 |  |
| V.1-a | 1 | 1 | 0.108 | 3.13 | 29 | 28.2 ± 8.5 |
|  | 2 | 1 | 0.182 | 3.93 | 22 |  |
|  | 3 | 2 | 0.132 | 4.54 | 34 |  |
|  | 4 | 3 | 0.097 | 2.53 | 26 |  |
|  | 5 | 4 | 0.055 | 2.33 | 42 |  |
|  | 6 | 3 | 0.104 | 2.51 | 24 |  |
|  | 7 | 4 | 0.213 | 3.36 | 16 |  |
|  | 8 | 5 | 0.137 | 2.75 | 20 |  |
|  | 9 | 5 | 0.151 | 2.03 | 13 |  |
|  | 10 | 6 | 0.081 | 2.86 | 35 |  |
|  | 11 | 6 | 0.091 | 3.32 | 36 |  |
|  | 12 | 7 | 0.147 | 5.14 | 35 |  |
|  | 13 | 7 | 0.158 | 5.20 | 33 |  |
| V.1-b | 1 | 1 | 0.109 | 1.22 | 11.2 | 9.8 ± 1.4 |
|  | 2 | 1 | 0.111 | 0.94 | 8.4 |  |
| 1-2 | 1 | 1 | 0.092 | 2.76 | 29.9 | 21.6 ± 5.9 |
|  | 2 | 1 | 0.094 | 1.69 | 18.1 |  |
|  | 3 | 1 | 0.119 | 2.01 | 16.9 |  |
| V.2-a | 1 | 1 | 0.083 | 9.56 | 114.8 | 57.2 ± 6.4 |
|  | 2 | 2 | 0.249 | 9.20 | 37.0 |  |
|  | 3 | 3 | 0.063 | 4.99 | 79.1 |  |
|  | 4 | 3 | 0.067 | 5.80 | 87.1 |  |
|  | 5 | 4 | 0.154 | 8.63 | 55.9 |  |
|  | 6 | 4 | 0.184 | 7.81 | 42.4 |  |
|  | 7 | 5 | 0.184 | 8.81 | 48.0 |  |

TABLE 2-continued

| Example | Measurement No. | Preparation No. | ACC 1 IC50 [μmol/l] | ACC 2 IC50 [μmol/l] | Ratio IC50s ACC2/ACC1 (respective measurement) | Selectivity ACC1 vs. ACC2 (mean of the individual measurements ± standard deviation) |
|---|---|---|---|---|---|---|
| | 8 | 6 | 0.090 | 3.99 | 44.5 | |
| | 9 | 4 | 0.087 | 2.14 | 24.8 | |
| | 10 | 4 | 0.075 | 2.90 | 38.5 | |
| V.2-b | 1 | 1 | 0.067 | 0.580 | 8.6 | 9.4 ± 0.8 |
| | 2 | 1 | 0.059 | 0.610 | 10.3 | |
| I-3 | 1 | 1 | 0.165 | 8.08 | 49.0 | 47.0 ± 2.1 |
| | 2 | 1 | 0.146 | 6.55 | 44.9 | |
| V.3-a | 1 | 1 | 0.108 | 3.13 | 28.9 | 28.2 ± 8.5 |
| | 2 | 1 | 0.182 | 3.93 | 21.6 | |
| | 3 | 2 | 0.132 | 4.54 | 34.4 | |
| | 4 | 3 | 0.097 | 2.53 | 26.1 | |
| | 5 | 4 | 0.055 | 2.33 | 42.3 | |
| | 6 | 3 | 0.104 | 2.51 | 24.2 | |
| | 7 | 4 | 0.213 | 3.36 | 15.7 | |
| | 8 | 5 | 0.137 | 2.75 | 20.1 | |
| | 9 | 5 | 0.151 | 2.03 | 13.4 | |
| | 10 | 6 | 0.081 | 2.86 | 35.2 | |
| | 11 | 6 | 0.091 | 3.32 | 36.5 | |
| | 12 | 7 | 0.147 | 5.14 | 35.1 | |
| | 13 | 7 | 0.158 | 5.20 | 33.0 | |
| V.3-b | 1 | 1 | 0.092 | 0.591 | 6.4 | 6.4 |
| I-4 | 1 | 1 | 0.104 | 4.35 | 41.7 | 30.8 ± 8.5 |
| | 2 | 1 | 0.133 | 4.06 | 30.6 | |
| | 3 | 2 | 0.131 | 3.05 | 23.3 | |
| | 4 | 2 | 0.116 | 3.82 | 33.1 | |
| | 5 | 3 | 0.084 | 3.30 | 39.0 | |
| | 6 | 3 | 0.123 | 2.12 | 17.2 | |
| V.4-a | 1 | 1 | 0.083 | 9.56 | 114.8 | 57.2 ± 26.4 |
| | 2 | 2 | 0.249 | 9.20 | 37.0 | |
| | 3 | 3 | 0.063 | 4.99 | 79.1 | |
| | 4 | 3 | 0.067 | 5.80 | 87.1 | |
| | 5 | 4 | 0.154 | 8.63 | 55.9 | |
| | 6 | 4 | 0.184 | 7.81 | 42.4 | |
| | 7 | 5 | 0.184 | 8.81 | 48.0 | |
| | 8 | 6 | 0.090 | 3.99 | 44.5 | |
| | 9 | 4 | 0.087 | 2.14 | 24.8 | |
| | 10 | 4 | 0.075 | 2.90 | 38.5 | |
| V.4-b | 1 | 1 | 0.073 | 1.118 | 15.2 | 15.2 |

These data show that the compounds without trans-methoxy group have a markedly poorer selectivity against human ACC2. Some related structures of the prior art having a trans-methoxy group in position 8 of the azaspiro[4.5]dec-3-en-2-one ring system also inhibit ACC1 strongly and are selective against ACC2. This property of the structures of the prior art was unknown, not obvious and not discoverable without unreasonable effort.

4.2 Cell Assays

Table 3 summarizes the cell assay results of working examples and comparative examples.

TABLE 3

| Example | KM12 IC50 (μmol/l) | PC3 IC50 (μmol/l) | H460 IC50 (μmol/l) | MCF7 IC50 (μmol/l) |
|---|---|---|---|---|
| I-1 | 0.021 | 0.029 | 0.088 | 0.026 |
| V.1-a | 0.038 | 0.035 | 0.079 | 0.023 |
| V.1-b | 0.037 | 0.038 | 0.057 | 0.035 |
| V.1-c | 0.827 | 0.275 | 1.870 | 0.288 |
| I-2 | 0.014 | 0.022 | 0.104 | <0.014 |
| V.2-a | 0.073 | 0.046 | 0.082 | 0.032 |
| V.2-b | 0.245 | 0.398 | 0.573 | 0.030 |
| V.2-c | 2.370 | 0.767 | 2.120 | 0.309 |
| I-3 | 0.222 | 0.194 | 0.365 | 0.045 |
| V.3-a | 0.038 | 0.035 | 0.079 | 0.023 |
| V.3-b | 0.031 | 0.036 | 0.067 | 0.023 |
| I-4 | 0.096 | 0.120 | 0.333 | 0.048 |

TABLE 3-continued

| Example | KM12 IC50 (μmol/l) | PC3 IC50 (μmol/l) | H460 IC50 (μmol/l) | MCF7 IC50 (μmol/l) |
|---|---|---|---|---|
| V.4-a | 0.073 | 0.046 | 0.082 | 0.032 |
| V.4-b | 0.035 | 0.030 | 0.043 | 0.020 |

4.3 ACC1 Expression in Tumour Tissue and Normal Tissue

The ACC1 expression in tumour tissue and corresponding normal tissue was determined by microarray (FIG. 1). In breast carcinomas, colorectal carcinomas, bronchial carcinomas and pancreas carcinomas, the expression of ACC1 was significantly upregulated compared to normal tissue.

4.4 Octanol/Water Distribution Coefficient (logP/D), Membrane Affinity (logMA) and Protein Binding to Human Serum Albumin ($K_d$ HSA)

Table 4 shows the logP/D, logMA and $K_d$ HSA values determined.

Evaluation of the HPLC peaks was carried out using Discovery Quant Analyze. The results (logMA and binding constant to HSA $K_d$) were calculated using an Excel workbook provided by Sovicell.

TABLE 4

| Example | logP/D pH7.4 | logMA | $K_d$ HSA [µmol/l] |
|---|---|---|---|
| 1-1 | 2.44 (2.4-2.5, n = 5) | 1.78 (1.6-1.9, n = 5) | 1.73 (1.32-2.16, n = 5) |
| V.1-a | 2.51 (2.4-2.6, n = 7) | 1.4 (0.9-1.7, n = 7) | 4.84 (3.66-6.18, n = 7) |
| V.1-b | 2.23 (1.8-2.5, n = 3) | 2.38 (2.0-2.7, n = 4) | 3.07 (2.38-2.8, n = 3) |
| V.1-c | 1.6 (n = 1) | 2.1 (n = 1) | 6.9 (n = 1) |
| 1-2 | 2.45 (2.4-2.5, n = 2) | 1.8 (n = 1) | 1.79 (n = 1) |
| V.2-a | 2.52 (2.5-2.6, n = 8) | 1.67 (1.2-1.9, n = 6) | 2.8 (2.42-3.67, n = 6) |
| V.2-b | 2.55 (2.4-2.7, n = 2) | 2.55 (2.4-2.7, n = 2) | 1.43 (1.16-1.7, n = 2) |
| V.2-c | 1.3 (n = 1) | 2.3 (n = 1) | 1.38 (n = 1) |
| 1-3 | 2.3 (n = 1) | <1.0 (n = 1) | 4.8 (n = 1) |
| V.3-a | 2.51 (2.4-2.6, n = 7) | 1.4 (0.9-1.7, n = 7) | 4.84 (3.66-6.18, n = 7) |
| V.3-b | 2.5 (2.5, n = 4) | 2.08 (1.9-2.3, n = 4) | 4.2 (3.41-4.89, n = 4) |
| 1-4 | 2.38 (2.3-2.4, n = 5) | 1.14 (0.9-1.3, n = 5) | 2.85 (1.96-3.4, n = 5) |
| V.4-a | 2.52 (2.5-2.6, n = 8) | 1.67 (1.2-1.9, n = 6) | 2.8 (2.42-3.67, n = 6) |
| V.4-b | 2.57 (2.5-2.6, n = 3) | 2.13 (2.1-2.2, n = 3) | 3.64 (2.48-5.18, n = 3) |

4.5 Plasma Protein Binding by Equilibrium Dialysis

Table 5 shows binding to plasma proteins of man, mouse and rat, determined by equilibrium analysis.

TABLE 5

| Example | fu [%] (human) | fu [%] (mouse) | fu [%] (rat) | fu (mouse)/fu (human) |
|---|---|---|---|---|
| 1-1 | 0.2 (0.18-0.23, n = 2) | 0.82 (0.75-0.88, n = 2) | — | 4 |
| V.1-a | 0.38 (0.33-0.44, n = 2) | 2.49 (2.35-2.62, n = 2) | 0.23 (n = 1) | 7 |
| V.1-b | 0.07 (n = 1) | 2.41 (n = 1) | — | 34 |
| V.1-c | — | — | — | — |
| 1-2 | 0.26 (n = 1) | 1.4 (1.29-1.51, n = 2) | — | 5 |
| V.2-a | 0.39 (n = 1) | 2.8 (n = 1) | 0.23 (0.22-0.25, n = 2) | 7 |
| V.2-b | 0.05 (n = 1) | 1.9 (n = 1) | — | 39 |
| V.2-c | — | — | — | — |
| 1-3 | 0.41 (0.40-0.42, n = 2) | 3.8 (3.57-4.02, n = 2) | — | 9 |
| V.3-a | 0.38 (0.33-0.44, n = 2) | 2.49 (2.35-2.62, n = 2) | 0.23 (n = 1) | 7 |
| V.3-b | 0.36 (0.35-0.38, n = 2) | 10.87 (10.4-11.3, n = 2) | 7.79<br>7.25-8.33 (n = 2) | 30 |
| 1-4 | 0.37 (0.37-0.38, n = 2) | 2.17 (2.06-2.28, n = 2) | 0.21 (n = 2) | 6 |
| V.4-a | 0.39 (n = 1) | 2.8 (n = 1) | 0.23 (0.22-0.25, n = 2) | 7 |
| V.4-b | 1.41 (n = 1) | 1.76 (n = 1) | 0.11 (n = 1) | 1 |

4.6 Pharmacokinetic Parameters

Pharmacokinetic Parameters Obtained from Rats.

Table 6 shows the pharmacokinetic parameters obtained from rats.

TABLE 6

| Example | $CL_{plasma}$ [l/h/kg] | $CL_{blood}$ [l/h/kg] | $t^{1/2}$ [h] | Vss [l/kg] | F [%] |
|---|---|---|---|---|---|
| 1-1 | 0.006 | 0.011 | 103 | 0.85 | 163 |
| V.1-a | 0.009 | — | 28 | 0.3 | 83 |
| V.1-b | — | — | — | — | — |
| V.1-c | — | — | — | — | — |
| 1-2 | 0.029 | 0.039 | 65 | 2.4 | 131 |
| V.2-a | 0.013 | — | 33 | 0.51 | 71 |
| V.2-b | — | — | — | — | — |
| V.2-c | — | — | — | — | — |
| 1-3 | 0.002 | 0.005 | 79 | 0.29 | 68 |
| V.3-a | 0.009 | — | 28 | 0.3 | 83 |
| V.3-b | — | — | — | — | — |
| 1-4 | 0.007 | 0.011 | 51 | 0.44 | 83 |
| V.4-a | 0.013 | — | 33 | 0.51 | 71 |
| V.4-b | — | — | — | — | — |

4.7 In-Vivo Efficacy

Maximum Tolerated Dose (MTD) in the Mouse

Examples 1-1, V.1-a/V.3-a, V.2-a/V.4-a and 1-4 were administered to female nude mice (NMRI nu/nu):

Dosage: see Table 7
Administration route: oral
Vehicle: PEG400/ethanol/Solutol HS 15 (70/5/25, v/v/v)
(Solutol HS15: polyoxyethylene ester of 12-hydroxystearic acid)

Administration volume: 10 ml/kg:

Protocol: see Table 7

The treatment phase was followed by an observation phase of 21 days. The deaths that occurred during this period and the effect on the body weight are summarized in Table 7.

TABLE 7

| Substance | Dose (mg/kg) | Protocol | Maximum change in body weight (%) | Deaths |
|---|---|---|---|---|
| 1-1 | 12.5 | 21 days, 1 administration per day | plus 12 | 0 of 4 |
| 1-1 | 25 | 21 days, 1 administration per day | plus 11 | 0 of 4 |
| 1-1 | 50 | 21 days, 1 administration per day | plus 10 | 1 of 4 |
| 1-1 | 75 | 21 days, 1 administration per day | plus 11 | 0 of 4 |
| 1-1 | 100 | 21 days, 1 administration per day | plus 16 | 0 of 4 |
| V.1-a/V.3-a | 25 | 21 days, 1 administration per day | plus 7 | 0 of 4 |
| V.1-a/V.3-a | 50 | 21 days, 1 administration per day | plus 17 | 0 of 4 |
| V.1-a/V.3-a | 100 | 21 days, 1 administration per day | plus 23 | 0 of 4 |

TABLE 7-continued

| Substance | Dose (mg/kg) | Protocol | Maximum change in body weight (%) | Deaths |
|---|---|---|---|---|
| V.2-a/V.4-a | 10 | 21 days, 1 administration per day | plus 21 | 0 of 4 |
| V.2-a/V.4-a | 20 | 21 days, 1 administration per day | plus 19 | 0 of 4 |
| V.2-a/V.4-a | 40 | 21 days, 1 administration per day | plus 17 | 0 of 4 |
| V.2-a/V.4-a | 80 | 21 days, 1 administration per day | minus 4 | 0 of 4 |
| 1-4 | 25 | 21 days, 2 administrations per day | plus 9 | 0 of 4 |
| 1-4 | 50 | 21 days, 2 administrations per day | plus 8 | 0 of 4 |
| 1-4 | 75 | 21 days, 2 administrations per day | plus 0 | 0 of 4 |
| 1-4 | 100 | 21 days, 2 administrations per day | plus 9 | 0 of 4 |
| 1-4 | 100 | 21 days, 1 administration per day | plus 13 | 0 of 4 |

Accordingly, the MTD for a 21-day treatment with administration once per day for Examples
1-1: is higher than 100 mg/kg
V.1-a/V.3-a: is higher than 100 mg/kg
V.2-a/V.4-a: is higher than 80 mg/kg
1-4: is higher than 100 mg/kg Accordingly, the MTD for a 21-day treatment with administration twice per day of Example 1-4 is higher than 100 mg/kg.

In-Vivo Efficacy in the PC3 Xenograft Model in the Mouse

Examples 1-1, V.1-a/V.3-a, 1-2, V.2-a/V.4-a and 1-4 were then administered to male nude mice (NMRI nu/nu) in the PC-3 prostate carcinoma xenograft model:
Dosage: see Table 8
Administration route: oral
Vehicle: PEG400/ethanol/Solutol HS 15 (70/5/25, v/v/v)
Administration volume: 10 ml/kg
Scheme: see Table 8
Number of mice: see Table 8

TABLE 8

| Substance | Dose (mg/kg) | Protocol | T/C | Maximum change in body weight (%) | Deaths |
|---|---|---|---|---|---|
| 1-1 | 80 | 15 days, 2 administrations per day | 0.34 | minus 5 | 0 of 10 |
| V.1-a/V.3-a | 100 | 14 days, 1 administration per day | 0.30 | minus 8 | 0 of 9 |
| V.1-a/V.3-a | 100 | 14 days, 2 administrations per day | 0.15 | minus 10 | 2 of 9 |
| 1-2 | 40 | 17 days, 2 administrations per day | 0.44 | plus 0 | 0 of 9 |
| 1-2 | 80 | 17 days, 2 administrations per day | 0.28 | minus 4 | 0 of 9 |
| V.2-a/V.4-a | 40 | 20 days, 1 administration per day | 0.71 | plus 5 | 0 of 9 |
| V.2-a/V.4-a | 80 | 20 days, 1 administration per day | 0.44 | plus 9 | 0 of 9 |
| V.2-a/V.4-a | 80 | 14 days, 2 administrations per day | 0.27 | minus 17 | 1 of 9 |
| 1-4 | 80 | 17 days, 2 administrations per day | 0.29 | minus 1 | 0 of 10 |

The therapeutic efficacy was defined as a T/C of <=0.50. Good tolerability was defined as a maximum change in body weight of <=minus 10% and 100% survival of the test animals. Accordingly, at 80 mg/kg and administration 2 times per day, therapeutic efficacy and good tolerability were observed for Example 1-1.

Accordingly, at 100 mg/kg and administration once per day, therapeutic efficacy and good tolerability were observed for Example V.1-a/V.3-a, whereas therapeutic efficacy, but no good tolerability, were observed at 100 mg/kg and administration 2 times per day.

Accordingly, at 40 mg/kg and at 80 mg/kg (administration in each case 2 times per day), therapeutic efficacy and good tolerability were observed for Example 1-2.

Accordingly, at 80 mg/kg and administration once per day, therapeutic efficacy and good tolerability were observed for Example V.2-a/V.4-a, whereas no therapeutic efficacy was observed at 40 mg/kg and administration once per day and no good tolerability was observed at 80 mg/kg and administration 2 times per day.

Accordingly, at 80 mg/kg and administration 2 times per day, therapeutic efficacy and good tolerability were observed for Example 1-4.

Prediction of Human Pharmacokinetic Parameters and Human Therapeutic Dosage

The human pharmacokinetic (PK) parameters (Table 9) were predicted based on the in vivo PK parameters obtained for rats (single species scaling), taking into account the interspecies differences in the free fraction (fu) in the plasma. The effective AUC (area under curve) was determined based on the measured plasma concentration time profile for in vivo efficacy in the PC3 tumour model of the mouse (nu/nu mouse). The therapeutic human dosage was determined using the predicted human clearance (CL), assuming 100% bioavailability (F=1) and using the effective AUC in the animal model according to the formula below:

$$\text{dosage} = AUC \times \frac{fu_{mouse}}{fu_{human}} \times \frac{CL}{F}$$

TABLE 9

| Ex. | dosage (mouse) [mg/kg] | ther. AUC (mouse) [mg * h/l] | fu (mouse/ human) | calc. AUC (human) [mg * h/l] | pred. CL (human) [l/h/kg] | pred. dosage (human) [mg/kg] | pred. dosage (human) [mg/patient] |
|---|---|---|---|---|---|---|---|
| 1-1 | 80 [2 × per day] | 289 | 4 | 1155 | 0.002 | 1.7 | 121 |
| V.1-a | 100 [1 × per day] | 984 | 6.6 | 6494 | 0.003 | 19.5 | 1365 |
|  | 100 [2 × per day] | 1495 |  | 9867 |  | 30 | 2072 |
| V.1-b | — | — | — | — | — | — | — |
| V.1-c | — | — | — | — | — | — | — |
| 1-2 | 40 [2 × per day] | 66 | 5.4 | 355 | 0.009 | 3.2 | 223 |
|  | 80 [2 × per day] | 156 |  | 842 |  | 7.6 | 531 |
| V.2-a | 80 [1 × per day] | 544 | 7 | 3737 | 0.006 | 24 | 1674 |
|  | 80 [2 × per day] | 672 |  | 4702 |  | 30 | 2106 |
| V.2-b | — | — | — | — | — | — | — |
| V.2-c | — | — | — | — | — | — | — |
| 1-3 | — | — | — | — | — | — | — |
| V.3-a | 100 [1 × per day] | 984 | 6.6 | 6494 | 0.003 | 19.5 | 1365 |
|  | 100 [2 × per day] | 1495 |  | 9867 |  | 30 | 2072 |
| V.3-b | — | — | — | — | — | — | — |
| 1-4 | 80 [2 × per day] | 712 | 5.8 | 4127 | 0.003 | 12.4 | 867 |
| V.4-a | 80 [1 × per day] | 544 | 7 | 3737 | 0.006 | 24 | 1674 |
|  | 80 [2 × per day] | 672 |  | 4702 |  | 30 | 2106 |
| V.4-b | — | — | — | — | — | — | — | ther. = therapeutic
calc. = calculated
pred. = predicted (fu-corrected)

FIGURES

FIG. 1: ACC1 expression in tumour tissue and corresponding normal tissue

The invention claimed is:

1. A compound of formula (I)

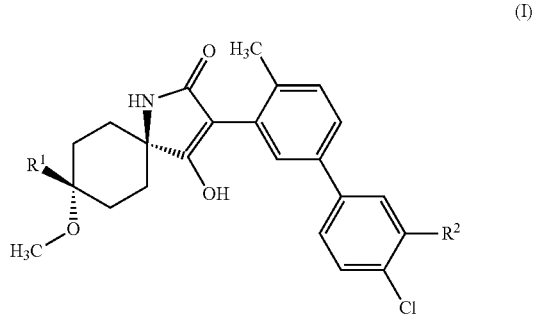

(I)

in which
R$^1$ represents a trifluoromethyl or methoxymethyl group and
R$^2$ represents hydrogen or fluorine,
or a salt thereof.

2. A compound selected from
(5r,8r)-3-(4'-chloro-3'-fluoro-4-methylbiphenyl-3-yl)-4-hydroxy-8-methoxy-8-(methoxymethyl)-1-azaspiro[4.5]dec-3-en-2-one;
(5r,8r)-3-(4'-chloro-4-methylbiphenyl-3-yl)-4-hydroxy-8-methoxy-8-(methoxymethyl)-1-azaspiro[4.5]dec-3-en-2-one;
(5r,8r)-3-(4'-chloro-3'-fluoro-4-methylbiphenyl-3-yl)-4-hydroxy-8-methoxy-8-(trifluoromethyl)-1-azaspiro[4.5]dec-3-en-2-one; and
(5r,8r)-3-(4'-chloro-4-methylbiphenyl-3-yl)-4-hydroxy-8-methoxy-8-(trifluoromethyl)-1-azaspiro[4.5]dec-3-en-2-one.

3. A pharmaceutical formulation comprising a compound according to claim 1 in combination with a further active compound, wherein the further active compound includes at least one of afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2.alpha., interferon-alpha-2.beta., interferon-alpha-n1, interferon-alpha-n3, interferon-beta, interferon-gamma-1.alpha., interleukin-2, intron A, iressa, irinotecan, kytril, lapatinib, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retic acid, satraplatin, seocalcitol, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, and zoledronic acid.

4. A pharmaceutical formulation comprising a compound according to claim 1 and a pharmaceutically acceptable excipient.

5. A method for the treatment of breast carcinomas, colorectal carcinomas, prostate carcinomas or non-small-cell bronchial carcinomas comprising administering to a human or other mammal in need thereof a therapeutically effective amount of a compound according to claim 1.

6. A method for the treatment of hormone receptor-positive breast carcinomas or androgen receptor-negative prostate carcinomas comprising administering to a human or other mammal in need thereof a therapeutically effective amount of a compound according to claim 1.

7. A method for the treatment of breast carcinomas, colorectal carcinomas, prostate carcinomas or non-small-cell bronchial carcinomas comprising administering to a human or other mammal in need thereof a therapeutically effective amount of a compound according to claim 2.

8. A method for the treatment of hormone receptor-positive breast carcinomas or androgen receptor-negative prostate carcinomas comprising administering to a human or other mammal in need thereof a therapeutically effective amount of a compound according to claim 2.

* * * * *